US005855812A

United States Patent [19]
Radcliffe et al.

[11] Patent Number: 5,855,812
[45] Date of Patent: *Jan. 5, 1999

[54] COMPOUNDS AND PROCESS FOR CONTROLLING CONE TILT ANGLE IN MIXTURES OF SMECTIC LIQUID CRYSTAL COMPOUNDS

[75] Inventors: Marc D. Radcliffe, Newport; Patricia M. Savu, Maplewood; Daniel C. Snustad, Woodbury; Terence D. Spawn, West Lakeland Township, all of Minn.

[73] Assignee: Minnesota Mining and Manufacturing Company, St. Paul, Minn.

[ * ] Notice: The term of this patent shall not extend beyond the expiration date of Pat. No. 5,658,491.

[21] Appl. No.: 827,753

[22] Filed: Apr. 11, 1997

[51] Int. Cl.$^6$ .......................... C09K 19/52; C09K 19/06; C09K 19/34; C07C 22/00

[52] U.S. Cl. .................. 252/299.01; 252/299.6; 252/299.61; 252/299.62; 252/299.63; 252/299.65; 252/299.66; 252/299.67; 570/144; 568/626; 568/647

[58] Field of Search .......................... 252/299.01, 299.6, 252/299.62, 299.63, 299.61, 299.65, 299.66, 299.67; 570/144; 568/627

[56] References Cited

U.S. PATENT DOCUMENTS

| | | | |
|---|---|---|---|
| 2,519,983 | 8/1950 | Simons | 204/62 |
| 3,470,258 | 9/1969 | Tesoro | 260/615 |
| 4,001,137 | 1/1977 | Steinstrasser | 252/299 |
| 4,011,173 | 3/1977 | Steinstrasser | 252/299 |
| 4,113,647 | 9/1978 | Coates et al. | 252/299 |
| 4,202,791 | 5/1980 | Sato et al. | 252/299 |
| 4,256,656 | 3/1981 | Beguim et al. | 260/465 |
| 4,330,426 | 5/1982 | Eidenschink et al. | 252/299.63 |
| 4,367,924 | 1/1983 | Clark et al. | 350/334 |
| 4,393,231 | 7/1983 | Misaki et al. | 560/73 |
| 4,400,293 | 8/1983 | Romer et al. | 252/299.63 |
| 4,411,494 | 10/1983 | Crossland et al. | 350/339 R |
| 4,419,664 | 12/1983 | Crossland et al. | 340/784 |
| 4,439,015 | 3/1984 | Rich et al. | 349/183 X |
| 4,481,149 | 11/1984 | Misaki et al. | 260/465 D |
| 4,528,562 | 7/1985 | Crossland et al. | 340/805 |
| 4,564,694 | 1/1986 | Hirai et al. | 560/1 |
| 4,572,794 | 2/1986 | Eidenschink et al. | 252/299.2 |
| 4,576,732 | 3/1986 | Isogai et al. | 252/299.65 |

(List continued on next page.)

FOREIGN PATENT DOCUMENTS

| | | | |
|---|---|---|---|
| 0 047 877 | 3/1982 | European Pat. Off. | C07C 103/375 |
| 0 163 299 | 12/1985 | European Pat. Off. | C09K 19/02 |
| 0 181 601 | 5/1986 | European Pat. Off. | C09K 19/60 |
| 0 220 747 | 5/1987 | European Pat. Off. | . |
| 0 332 025 | 9/1989 | European Pat. Off. | C07C 121/407 |
| 0 548 548 | 6/1993 | European Pat. Off. | G02F 1/137 |
| 0 641 850 | 3/1995 | European Pat. Off. | C09K 19/04 |
| 33 32 692 | 3/1985 | Germany | C08C 121/46 |
| 40 34 123 | 4/1992 | Germany | C07C 19/08 |
| 4222371 | 1/1994 | Germany | C07C 43/225 |
| 57-165334 | 10/1982 | Japan | C09K 3/34 |
| 1-104031 | 4/1989 | Japan | C07C 69/63 |
| 2-69443 | 3/1990 | Japan | C07C 69/92 |
| 2 162 515 | 2/1986 | United Kingdom | C07C 69/773 |
| WO 88/03530 | 5/1988 | WIPO | C07D 239/26 |
| WO 88/05803 | 8/1988 | WIPO | C09K 19/52 |
| WO 88/08441 | 11/1988 | WIPO | C09K 19/30 |
| WO 91/00897 | 1/1991 | WIPO | C09K 19/34 |
| WO 91/11418 | 8/1991 | WIPO | C07C 22/08 |

OTHER PUBLICATIONS

Jager et al., "Synthesis of Amino Sugars via Isoxazolines: D–Allosamine," Synthesis, pp. 556–560 (1990).

Chaudhary et al., "A Simplified Procedure for the Preparation of Triphenylmethylethers," Tetrahedron Letters, pp. 95–98 (1979).

Middleton, "New Fluorinating Reagents. Dialkylaminosulfur Fluorides," J. Org. Chem. vol. 40, No. 5, pp. 574–578 (1975).

Sakaguchi et al., "New Materials for Ferroelectric Liquid Crystals. Novel Compounds Containing Chiral $\gamma$–Lactone Ring," Ferroelectrics, vol. 114, pp. 265–272 (1991).

Fukuda et al., "Antiferroelectric Chiral Smectic Liquid Crystals," J. Mater. Chem, vol. 4, pp. 997–1016 (1994).

Naciri et al., "Effect of Chiral End Group Variation of the Properties of Ferroelectric Copolymers," Ferroelectrics, vol. 148, pp. 297–310 (1993).

Pelzl et al., "Field–induced Colour Change of Liquid Crystalline Dyes," Kristall und Technik, vol. 14, pp. 817–823 (1979).

Pelzl et al., "Freedericksz Transition of Planar Oriented Smectic C Phases," Liquid Crystals, vol. 2, No. 2, pp. 131–148 (1987).

(List continued on next page.)

Primary Examiner—C. H. Kelly
Attorney, Agent, or Firm—Lucy C. Weiss

[57] ABSTRACT

A process for controlling the cone tilt angle of a tilted smectic liquid crystal composition comprises the step of combining (a) at least one liquid crystal composition comprising at least one smectic or latent smectic liquid crystal compound comprising (i) an aliphatic fluorocarbon terminal portion comprising a terminal fluoroalkyl or fluoroether group and an alkylene group having at least two carbon atoms and containing at least one catenary ether oxygen atom, (ii) an aliphatic hydrocarbon terminal portion, and (iii) a central core connecting the terminal portions, wherein the alkylene group of the aliphatic fluorocarbon terminal portion is directly linked to the central core by a moiety selected from the group consisting of a covalent bond, —CH═CH—, and —C≡C—; and (b) at least one liquid crystal composition comprising at least one smectic or latent smectic liquid crystal compound; with the provisos that at least one of the compositions (a) and (b) comprises at least one chiral liquid crystal compound and that the combining of compositions (a) and (b) provides an optically active, tilted chiral smectic liquid crystal composition. The process enables control of cone tilt angle and thereby control of the brightness characteristics of liquid crystal display devices.

34 Claims, No Drawings

U.S. PATENT DOCUMENTS

| | | | |
|---|---|---|---|
| 4,592,858 | 6/1986 | Higuchi et al. | 252/299.66 |
| 4,613,209 | 9/1986 | Goodby et al. | 350/350 S |
| 4,614,608 | 9/1986 | Le Barney et al. | 252/299.64 |
| 4,617,140 | 10/1986 | Eidenschink et al. | 252/299.61 |
| 4,668,427 | 5/1987 | Saito et al. | 252/299.66 |
| 4,780,242 | 10/1988 | Miyazawa et al. | 252/299.65 |
| 4,816,178 | 3/1989 | Katagiri et al. | 252/299.6 |
| 4,816,596 | 3/1989 | Langlois | 358/423 |
| 4,837,364 | 6/1989 | Desbois et al. | 568/43 |
| 4,876,027 | 10/1989 | Yoshinaga et al. | 252/299.65 |
| 4,879,060 | 11/1989 | Shionozaki et al. | 252/299.61 |
| 4,886,619 | 12/1989 | Janulis | 252/299.1 |
| 4,914,224 | 4/1990 | Shoji et al. | 560/65 |
| 5,051,527 | 9/1991 | Suzuki et al. | 560/51 |
| 5,062,691 | 11/1991 | Tristani-Kendra et al. | 359/56 |
| 5,082,587 | 1/1992 | Janulis | 252/299.01 |
| 5,141,669 | 8/1992 | Bloom et al. | 252/299.65 |
| 5,167,859 | 12/1992 | Wachtler et al. | 252/299.61 |
| 5,194,179 | 3/1993 | Suzuki et al. | 252/299.66 |
| 5,196,140 | 3/1993 | Poetsch et al. | 252/299.01 |
| 5,252,695 | 10/1993 | Niciri et al. | 528/30 |
| 5,262,082 | 11/1993 | Janulis et al. | 252/299.01 |
| 5,348,677 | 9/1994 | Poetsch et al. | 252/299.6 |
| 5,362,919 | 11/1994 | Costello et al. | 568/601 |
| 5,377,033 | 12/1994 | Radcliffe | 359/75 |
| 5,399,291 | 3/1995 | Janulis et al. | 252/299.01 |
| 5,417,883 | 5/1995 | Epstein et al. | 262/299.01 |
| 5,437,812 | 8/1995 | Janulis et al. | 252/299.01 |
| 5,474,705 | 12/1995 | Janulis et al. | 252/299.01 |
| 5,482,650 | 1/1996 | Janulis et al. | 252/299.01 |
| 5,626,793 | 5/1997 | Reiffenrath et al. | 252/299.63 |
| 5,653,923 | 8/1997 | Nakamura et al. | 252/299.01 |
| 5,658,491 | 8/1997 | Kistner et al. | 252/299.01 |

OTHER PUBLICATIONS

Sierra et al., "Synthesis and Study of New α–Haloacid Ferroelectric Liquid Crystal Derivatives. MM2 Approach to the Molecular Structure–Ferroelectric Activity Relationship," Am. Chem. Soc., vol. 114, No. 20, pp. 7645–7651 (1992).

Meyer et al., "Ferroelectric Liquid Crystals," J. Physique, vol. 36, pp. L–69–L–71 (1975).

Zaschke et al., "Synthese niedrigschmelzender Kristallin–Flussiger Hetercyclen; 5–n–Alkyl–2–[4–n–alkanoyloxy–phenyl]pyrimidine," Z. Chem. vol. 15, pp. 441–441 (1975).

Mochizuki et al., "A High Contrast SSFLC Display Utilizing Naphtalene Base Liquid Crystal Materials and Conductive Orientation Films," SPIE, vol. 1665, pp. 102–113 (1992).

Pelzl et al., "Tilt Angle Determination of a Smectic C Phase by Field–Induced Freedericksz Transition and X ray Investigations," Mol. Cryst. Liq Cryst., vol. 53, pp. 167–179 (1979).

Clark et al., "Submicrosecond Bistable Electro–Optic Switching in Liquid Crystals," Appl. Phys. Lett., vol. 36, pp. 899–901 (1980).

Holy et al., "Nucleic Acid Components and Their Analogues. CLVIII. Preparation of Some Substituted 2–Amino– and 2–Mercaptopyrimidines from Trimethinium Salts," Collection Chzechoslov. Chem. Commun., vol. 38, pp. 1371–1381 (1973).

Kahn, "Laser–addressed Thermo–Optic Smectic Liquid–Crystal Storage Displays," Appl. Phys. Lett., vol. 22, No. 3, pp. 111–113 (1973).

Lagerwall et al., 1st International Symposium On Ferroelectric Liquid Crystals, Bordeaux–Arcachon, France (1987).

Partridge et al., "Amidines. Part IV. Preparation of Amidines from Cyanides and Ammonium Thiocyanate or Substituted Ammonium Thiocyanates," J. Chem. Soc., pp. 390–394 (1947).

Savu, "Perfluoroalkanesulfonic Acids," Kirk–Othmer Encyclopedia of Chemical Technology, Fourth Edition, vol. 11, pp. 558–564, John Wiley & Sons, New York (1994).

Knunyants et al., "Polyfluorinated Linear Bifunctional Compounds (Containing Like Functions) as Potential Monomers," Advances in Chem. (Uspekhi Khimi) vol. 32, original 1502, Eng. Trans, 461–476 (1963) Translation RSIC–165 (Redstone Information Center).

Arnold et al., "Synthetische Reaktionen Von Dimethylformamid I. Allegemeine Synthese Von β–Dialdehyden," Coll. Czech. Chem. Commun., vol. 23, pp. 452–461 (1958).

Abe et al., "Electrochemical Fluorination (Simons Process) as a Route to Perfluorinated Organic Compounds of Industrial Interest," Preparation, Properties and Industrial Applications of Organofluorine Compounds, pp. 20–41 (1982).

Patent Abstracts of Japan, vol. 15, No. 271 (C–0848), Jul. 10, 1991.

Titov et al., "Synthesis and Mesomorphism of Aryl ρ–Fluoralkyl(alkoxy)benzoates," Mol. Cryst. Liq. Cryst., vol. 47, pp. 1–5 (1978).

Ivashchenko et al., "New Mesogenic Compounds with a Large Dielectric Anisotropy," Mol. Cryst. Liq. Cryst., vol. 67, pp. 235–240 (1981).

Efron et al., "The Silicon Liquid–Crystal Light Valve," J. Appl. Phys., vol. 57(4), pp. 1356–1368 (1985).

Mahler, "Smectic Liquid Crystal from (Perfluorodecyl)Decane," Mol. Cryst. Liq. Cryst., vol. 2(3–4), pp. 111–119 (1985).

Decobert et al., "Synthesis and Mesomorphysm of Some New Ferro–Electric Smectic Liquid Crystals," Mol. Cryst. Liq. Cryst., vol. 114, pp. 237–247 (1984).

Eaton et al., "Studies in Organophosphorus Chemistry. I. Conversion of Alcohols and Phenols to Halides by Tertiary Phosphone Dihalides," J. Am. Chem. Soc., vol. 86, pp. 964–965 (1964).

Kondo et al., "New Room–Temperature Ferroelectric Liquid Crystals—Material Constants and Electro–Optic Properties–," Jap. Journal of Applied Physics, vol. 24, No. 11, pp. 1389–1393 (1985).

Gray, "Mesophases Formed by Non–Amphiphilic Systems," Liquid Crystals & Plastic Crystals, vol. 1, pp. 142–143, Ellis Horwood Limited (1974).

Zverkova et al., "Synthesis and Mesomorphism of ρ–fluoralky(alkoxy)benzoic esters," Advances in Liquid Crystal Research & Applications, Pergamon Press, Oxford, pp. 991–995 (1980).

Le Barny et al., "Mesmorphic Properties of Some New Fluorinated Liquid Crystals: the 4–n–Alkoxyperfluorobenzoate Series and Trifluoromethylbiphenyl Derivatives," Mol. Cryst. and Liq. Cryst., vol. 127, pp. 413–429 (1985).

Streitweiser et al., "Reaction with Alcohols," Introduction to Organic Chemistry, pp. 378–380, 480 and 837, Macmillan Publishing Co., New York (1976).

Sirutkaitis et al., "Polyfluoro–Subsituted Liquid Crystals," Advances in Liquid Crystal Research and Applications, Pergamon Press, Oxford, pp. 1023–1028 (1980).

Schiller et al., "Bistability and Domain Wall Motion in Smectic C Phases Induced by Strong Electric Fields," Liquid Crystals, vol. 2, No. 1, pp. 21–30 (1987).

Byun et al., "A Two–Step Synthesis of (R)– and (S)–Benzylglycidyl Ether," Tetrahedron Letters, vol. 30, No. 21, pp. 2751–2754 (1989).

Gray et al., "The Synthesis and Transition Temperatures of Some 4,4"–Dialkyl– and 4,4"–Alkoxyalkyl–1,1':4',1"–terphenyls with 2,3– or 2',3'–Difluoro Substituents and of their Biphenyl Analogues," J. Chem. Soc., Perkin Trans. II, pp. 2041–2053 (1989).

Iwakura et al., "Glycidyl Ether Reactions with Urethanes and Ureas. A New Synthetic Method for 2–Oxazolidones," J. Org. Chem, vol. 29, pp. 379–382 (1964).

Miyasato et al., "Direct Method with Triangular Waves for Measuring Spontaneous Polarization in Ferroelectric Liquid Crystals," Jap. J. Appl. Phys. vol. 22, No. 10, pp. L661–L663 (1983).

Nohira et al., "Synthesis and Mesomorphic Properties of Ferroelectric Liquid Crystals with a Fluroinated Asymmetric Frame (1)," Mol. Cryst. Liq. Cryst. vol. 180B, pp. 379–388 (1990).

COMPOUNDS AND PROCESS FOR CONTROLLING CONE TILT ANGLE IN MIXTURES OF SMECTIC LIQUID CRYSTAL COMPOUNDS

FIELD OF THE INVENTION

This invention relates to a process for preparing mixtures of smectic or latent smectic liquid crystal compounds having a controlled cone tilt angle. In other aspects, this invention relates to fluorinated, smectic or latent smectic liquid crystal compounds useful in the process; to mixtures prepared by the process; and to electrooptical display devices containing the mixtures.

BACKGROUND OF THE INVENTION

Devices employing liquid crystals have found use in a variety of electrooptical applications, in particular those which require compact, energy-efficient, voltage-controlled light valves, e.g., watch and calculator displays, as well as the flat-panel displays found in portable computers and compact televisions. Liquid crystal displays have a number of unique characteristics, including low voltage and low power of operation, which make them the most promising of the non-emissive electrooptical display candidates currently available.

One of the most important characteristics of a liquid crystal display device is its response time, i.e., the time required for the device to switch from the on (light) state to the off (dark) state. In a ferroelectric or anti-ferroelectric device, response time ($\tau = \eta \sin^2 \eta / P_s E$) is proportional to the rotational viscosity ($\eta$) of the liquid crystal compound(s) contained within the device, is also proportional to the square of the sine of the cone tilt angle ($\eta$) of a tilted smectic mesophase of the compounds, and is inversely proportional to the polarization ($P_s$) of the compounds and to the applied electric field (E). Thus, response time can be reduced by using compound(s) having high polarizations and/or low viscosities and/or low cone tilt angles, and such compounds are greatly desired in the art.

Other important characteristics of a liquid crystal display device are its brightness and contrast ratio. High brightness and contrast ratios provide enhanced optical discrimination and viewing ease and are therefore preferred. Brightness is related to the intensity of light transmitted through a device, which for a surface-stabilized ferroelectric device (as described in U.S. Pat. No. 4,367,924, the description of which is incorporated by reference herein) with two polarizers can be represented by the equation $I = I_o (\sin^2(4\eta))(\sin^2(\pi \Delta nd/\lambda))$, where $I_o$=transmission through parallel polarizers, $\eta$=liquid crystal cone tilt angle, $\Delta n$=liquid crystal birefringence, d=device spacing, and $\lambda$=wavelength of light used. The maximum transmission is obtained when both the terms $\sin^2(4\eta)$ and $\sin^2(\pi \Delta nd/\lambda)$ are at a maximum (each term equals one). Since the first term is at a maximum when the liquid crystal composition in the device has a cone tilt angle of 22.5 degrees, liquid crystal compounds which have cone tilt angles close to 22.5 degrees (or which can be mixed with other liquid crystal compounds to form compositions having cone tilt angles close to 22.5 degrees) are also highly desired in the art.

In particular, since many fluorine-containing liquid crystal compounds have cone tilt angles which exceed the optimum value of 22.5 degrees, materials and methods for reducing cone tilt angle are needed. Although hydrocarbon liquid crystal compounds have low cone tilt angles (below 22.5degrees), they generally cannot be used for this purpose due to their incompatibility with fluorine-containing liquid crystal compounds (which generally leads to loss of the active mesophase).

In addition to fast response times and optimized tilt angles, liquid crystal compounds should ideally possess broad smectic temperature ranges (to enable operation of a display device over a broad range of temperatures) or should be capable of combination with other liquid crystal compounds without adversely affecting the smectic phase behavior of the base mixture.

SUMMARY OF THE INVENTION

It has been discovered that the cone tilt angle of certain fluorine-containing liquid crystal compounds can surprisingly be reduced (and the smectic C mesophase often surprisingly broadened) by inserting an extended hydrocarbon ether group adjacent to a terminal fluoroalkyl or fluoroether group, i.e., between a central core and at terminal fluoroalkyl or fluoroether group. It has also been discovered that such compounds (as well as those which alone do not exhibit a smectic C mesophase) can be used in admixture with certain other liquid crystal compounds to control or adjust the cone tilt angle of the resultant mixture without significant adverse effect on the smectic C mesophase of the base composition.

It has now been further discovered that such compounds surprisingly exhibit particularly good mesophase transition temperature behavior (and are thus particularly useful in a process for controlling cone tilt angle) when the extended hydrocarbon ether group is directly linked to the central core by a moiety selected from the group consisting of a covalent bond, —CH=CH—, and —C≡C—. The compounds having this structural characteristic (hereinafter, "directly linked compounds") generally exhibit a transition from isotropic to smectic A at a considerably lower temperature than do the corresponding compounds having a more complex linking group between the central core and the extended hydrocarbon ether group. In addition, some directly linked compounds exhibit a lower temperature transition from smectic C to crystalline (K, the freezing point).

Thus, in one aspect, this invention provides a process for controlling the cone tilt angle of a tilted smectic liquid crystal composition while substantially maintaining or even improving the temperature range of the tilted smectic mesophase of the composition. The process comprises the step of combining (a) at least one liquid crystal composition comprising at least one smectic or latent smectic liquid crystal compound comprising (i) an aliphatic fluorocarbon terminal portion comprising a terminal fluoroalkyl or fluoroether group and an alkylene group having at least two carbon atoms and containing at least one catenary (i.e., in-chain and bonded only to carbon atoms) ether oxygen atom, (ii) an aliphatic hydrocarbon terminal portion, and (iii) a central core connecting the terminal portions, wherein the alkylene group of the aliphatic fluorocarbon terminal portion is directly linked to the central core by a moiety selected from the group consisting of a covalent bond, —CH=CH—, and —C≡C—; and (b) at least one liquid crystal composition comprising at least one smectic or latent smectic liquid crystal compound; with the provisos that at least one of the compositions (a) and (b) comprises at least one chiral liquid crystal compound and that the combining of compositions (a) and (b) provides an optically active, tilted chiral smectic liquid crystal composition. (Latent smectic liquid crystal compounds are those which by themselves may not exhibit certain smectic mesophase(s), e.g., tilted smectic mesophase(s), but which, when in admixture with compounds having smectic mesophases or with other compounds having latent smectic mesophases, develop or exhibit smectic mesophases under appropriate conditions.) Preferably, the former composition(s) (i.e., composition(s) (a)) are utilized in amount(s) such that the resulting combination has a cone tilt angle between about 10 and about 35 degrees. Composition(s) (b) preferably comprise at least one fluorine-containing liquid crystal compound.

The process of the invention enables control of cone tilt angle and thereby control of the brightness characteristics of liquid crystal display devices. The particularly good mesophase transition temperature behavior of the compounds used in the process enables the filling and operation of the display devices at lower temperatures (due to the above-referenced lower temperature transitions from isotropic to smectic A and from smectic C to crystalline, respectively). Thermal degradation of other device components (e.g., electronic or adhesive components) can thus be presented or minimized, and devices can be processed (i.e., heated to a temperature above the isotropic temperature at a certain heating rate, filled, and then cooled to a lower temperature at a certain cooling rate) more quickly and with less energy input. Furthermore, the lower temperature smectic A to smectic C transitions sometimes exhibited by the compounds enhance the capability of meeting electrooptic switching requirements (e.g., minimum viscosity for high speed).

The process of the invention is especially useful for reducing cone tilt angle in mixtures of fluorine-containing, smectic or latent smectic liquid crystal compounds (preferably compounds having fluorinated terminal portions, such as those compounds disclosed, for example, in U.S. Pat. Nos. 4,886,619 (Janulis), 5,082,587 (Janulis), 5,262,082 (Janulis et al.), 5,399,291 (Janulis et al.), and 5,437,812 (Janulis et al.) and in U.S.S.N. 08/338,957 (Janulis et al.) and U.S.S.N. 08/338,961(Janulis et al.), as well as compounds having at least one chiral, fluorinated terminal portion) . The compounds used in the process of the invention (in compositions) (a)), unlike hydrocarbon liquid crystal compounds, in many cases show excellent compatibility with such fluorine-containing liquid crystal compounds, show a beneficial effect or only a minimal negative effect on the smectic C temperature range of the resulting mixtures (even when present at high concentrations), and provide tilted chiral smectic mixtures having low viscosity and fast electrical response times over broad temperature ranges. In addition, many of the compounds have broad smectic C temperature ranges, making them useful alone, as well as in admixture with other liquid crystal compounds (as dopants or as the major components) , for electrooptical display applications.

In other aspects, this invention also provides fluorine-containing, smectic or latent smectic liquid crystal compounds useful in the process of the invention; mixtures comprising the compounds; mixtures prepared by the process of the invention; and electrooptical display devices containing the compounds or the mixtures.

DETAILED DESCRIPTION OF THE INVENTION

Compositions suitable for use (as composition(s) (a)) in the process of the invention are liquid crystal compositions which comprise at least one smectic or latent smectic liquid crystal compound comprising (i) an aliphatic fluorocarbon terminal portion comprising a terminal fluoroalkyl or fluoroether group and an alkylene group having at least two carbon atoms and containing at least one catenary ether oxygen atom, (ii) an aliphatic hydrocarbon terminal portion, and (iii) a central core connecting the terminal portions; wherein the alkylene group of the aliphatic fluorocarbon terminal portion is directly linked to the central core by a moiety selected from the group consisting of a covalent bond, —CH═CH—, and —C≡C—. Such smectic compounds exhibit surprisingly lower cone tilt angles and, in many cases, surprisingly broader smectic C mesophase, than corresponding compounds which do not have such an alkylene group (having at least two carbon atoms and containing at least one catenary ether oxygen) in the aliphatic fluorocarbon terminal portion. The aliphatic fluorocarbon terminal portion of the compounds can be represented by the formula —D—$R_h$—$R_f$, where $R_h$ is an alkylene group having at least two carbon atoms and containing at least one catenary ether oxygen atom; $R_f$ is fluoroalkyl (preferably, perfluoroalkyl) or fluoroether (preferably, perfluoroether); and D is a moiety selected from the group consisting of a covalent bond, —CH═CH—, and —C≡C—. When the $R_f$ group of the fluorocarbon terminal portion is perfluoroalkyl or perfluoroether, it can contain small amounts of residual carbon-bonded hydrogen atoms but is preferably completely fluorinated. Preferably, $R_f$ is perfluoroalkyl or perfluoroether (more preferably, perfluoroether) and contains from 1 to about 20 carbon atoms (more preferably, from about 4 to about 12 carbon atoms). $R_h$ preferably contains from 2 to about 14 carbon atoms (more preferably, from 2 to about 10).

The central core of the compounds generally comprises at least one or two rings independently selected from the group consisting of aromatic, heteroaromatic, alicyclic, substituted aromatic, substituted heteroaromatic, and substituted alicyclic rings, the rings being connected one with another by a covalent bond or by chemical groups selected from the group consisting of —COO—, —COS—, —HC═N—, —CH═CH—, —C≡C—, and —COSe—. The rings can be fused or non-fused. The heteroatoms within the heteroaromatic rings comprise at least one atom selected from the group consisting of nitrogen, oxygen, and sulfur. Non-adjacent ring carbon atoms in the alicyclic rings can be substituted by nitrogen, oxygen, or sulfur atoms.

A class of liquid crystal compounds which can be utilized (e.g., in composition(s) (a)) in the process of the present invention can be represented by the general formula I:

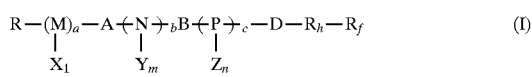  (I)

where M, N, and P are each independently selected from the group consisting of

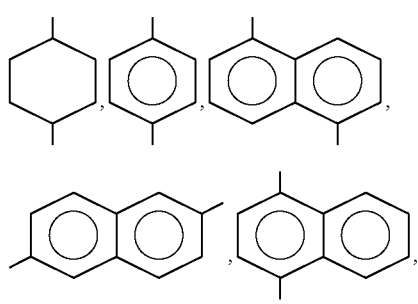

-continued

[chemical structures]

a, b, and c are each independently zero or an integer of from 1 to 3, with the proviso that the sum of a +b +c be at least 1;

each A and B are non-directionally and independently selected from the group consisting of a covalent bond, —C(=O)—O—, —C(=O)—S—, —C(=O)—Se—,
—C(=O) —Te—, —(CH$_2$CH$_2$—)$_k$—where k is 1 to 4,
—CH=CH—, —C≡C—, —CH=N—, —CH$_2$—O—,
—C(=O)—, and —O —;

each X, Y, and Z are independently selected from the group consisting of —Cl, —F, —Br, —I, —OH, —OCH$_3$, —CH$_3$, —CF$_3$, —OCF$_3$, —CN, and —NO$_2$;

each l, m, and n are independently zero or an integer of 1 to 4;

D is a moiety selected from the group consisting of a covalent bond, —CH=CH—, and —C≡C —;

R is selected from the group consisting of

—O—((C$_q$H$_{2q'-v'}$—(R')$_{v'}$) —O)$_w$—C$_q$H$_{2q+1-v}$—(R')$_v$,

—((C$_q$H$_{2q'-v'}$—(R')$_{v'}$)—O)$_w$—C$_q$H$_{2q+1-v}$—(R')$_v$,

—C(=O)—O—C$_q$H$_{2q+1-v}$—(R')$_v$, —O—(O=) C—C$_q$H$_{2q+1-v}$—(R')$_v$,

[D' ring structure] —W⟨D'⟩W—C$_q$H$_{2q+1-v}$—(R')$_v$,

—CR'H—(D')$_g$—CR'H—C$_q$H$_{2q+1-v}$—(R')$_v$, where each R' is independently selected from the group consisting of —Cl, —F, —CF$_3$, —NO$_2$, —CN, —H, —C$_q$H$_{2q+1}$, —O—(O=) C—C$_q$H$_{2q+1}$, —C(=O) —O—C$_q$H$_{2q+1}$, —Br, —OH, and —OC$_q$H$_{2q+1}$ (preferably, —H or —F); q' is independently an integer of 1 to about 20 for each (C$_q$H$_{2q'}$—O); q is an integer of 1 to about 20; w is an integer of 0 to about 10; v is an integer of 0 to about 6; each v' is independently an integer of 0 to about 6; g is an integer of 1 to about 3; each D' is independently and non-directionally selected from the group consisting of a covalent bond, —C(=O) —O—C$_r$H$_{2r}$—, —O—C$_r$H$_{2r}$—, —O—(O=)C—C$_r$H$_{2r}$—, —C≡C—, —CH=CH—, —C(=O)—, —O—(C$_s$H$_{2s}$O)$_t$C$_r$H$_{2r}$—, —C$_r$H$_{2r}$—, —(C$_s$H$_{2s}$)$_t$C$_r$H$_{2r}$—, —O—, —S—, —C$_r$H$_{2r}$—N—SO$_2$—, —N(C$_p$H$_{2p+1}$)—,
   |
   C$_p$H$_{2p+1}$ —C$_r$H$_{2r}$—N—C(=O)—, —CH=N—,
   |
   C$_p$H$_{2p+1}$ r and r' are independently integers of 0 to about 20, s is independently an integer of 1 to about 10 for each (C$_s$H$_{2s}$O), t is an integer of 1 to about 6, and p is an integer of 0 to about 4, with the proviso that the ring containing D' has from about 3 to about 10 ring atoms; each W is independently selected from the group consisting of N, CR', and SiR';

R$_h$ is an alkylene group having at least two carbon atoms (preferably, from 2 to about 14 carbon atoms; more preferably, from 2 to about 10) and containing at least one catenary ether oxygen atom; and R$_f$ is fluoroalkyl or fluoroether (preferably, perfluoroalkyl or perfluoroether; more preferably, perfluoroether) and preferably contains from 1 to about 20 carbon atoms (more preferably, from about 4 to about 12 carbon atoms).

Particularly preferred R$_h$ moieties can be represented by the general formula —(C$_s$H$_{2s}$O)$_t$C$_r$H$_{2r}$—, wherein s is independently an integer of 1 to about 10 for each (C$_s$H$_{2s}$O) (preferably, about 2 to about 7), t is an integer of 1 to about 6 preferably, 1 to about 3), and r' is an integer of 1 to about 10 (preferably, 1).

In defining R$_f$, particularly preferred fluoroalkyl groups are those which can be represented by the formula —C$_q$F$_{2q}$X', where q is as defined above (and, preferably, is at least about 3) and X' is hydrogen or fluorine. Other useful fluoroalkyl and fluoroether groups are those which can be represented by the formula —$R_f'$—$R_h'$, where $R_f'$ is a linear or branched, perfluorinated or partially-fluorinated alkylene group having from 1 to about 10 (preferably, from about 2 to about 6) carbon atoms and optionally containing one or more catenary, i.e., in-chain, ether oxygen atoms, and $R_h'$ is a linear or branched alkyl group having from 1 to about 14 (preferably, from about 3 to about 10) carbon atoms and optionally containing one or more catenary ether oxygen atoms. Preferably, $R_f'$ is perfluorinated, both $R_h'$ and $R_f'$ are linear, and at least one of the groups $R_h'$ and $R_f'$ contains at least one catenary ether oxygen atom. More preferably, $R_h'$ or both $R_h'$ and $R_f'$ contains at least one catenary ether oxygen atom.

Particularly preferred perfluoroether groups are those which can be represented by the formula —$(C_xF_{2x}O)_zC_yF_{2y+1}$, where x is independently an integer of 1 to about 10 for each $(C_xF_{2x}O)$, y is an integer of 1 to about 10, and z is an integer of 1 to about 10. Preferably, the perfluoroether group is linear, x is independently an integer of 1 to about 8 for each $(C_xF_{2x}O)$, y is an integer of 1 to about 6, and z is an integer of 1 to about 6.

Many of the perfluoroether group-containing liquid crystal compounds used in the process of the invention when used alone or when mixed with each other or with other fluorine-containing liquid crystal compounds (preferably, the perfluoroether group-containing liquid crystal compounds described in U.S. Pat. Nos. 5,262,082 (Janulis, et al.) and 5,437,812 (Janulis et al.) and in U.S.S.N. 08/338,957 (Janulis et al.) and U.S.S.N. 08/338,96 (Janulis et al.), the descriptions of which are incorporated herein by reference) exhibit a reduced temperature dependence of the smectic interlayer spacing. This property provides for the spontaneous generation of a bookshelf type layer structure, which is ideal for a tilted chiral smectic liquid crystal device.

A preferred subclass of liquid crystal compounds for use in the process of the invention (e.g., in composition(s) (a)) are those compounds which can be represented by formula I, supra, wherein $R_f$ is fluoroether (preferably, perfluoroether) and $R_h$ is represented by the directional general formula —$(C_sH_{2s}O)_tC_rH_{2r}$—, wherein s is independently an integer of 2 to about 10 (preferably, 3 to about 10; more preferably, 3 to about 7) for each $(C_sH_{2s}O)$, t is an integer of 1 to about 6 (preferably, 1 to about 3; more preferably, 1 to 2), and r' is an integer of 1 to about 10 (preferably, 1 to about 5; more preferably, 1); with the proviso that the compounds exhibit at least one tilted smectic mesophase. Preferably, $R_h$ has from about 3 to about 14 carbon atoms (more preferably from about 4 to about 10).

Another preferred subclass of liquid crystal compounds for use in the process of the invention (e.g., in composition(s) (a)) are those compounds which can be represented by formula I, supra, wherein $R_f$ is fluoroether (preferably, perfluoroether) and $R_h$ is represented by the directional general formula —$(C_sH_{2s}O)_tC_rH_{2r}$—, wherein s is independently an integer of 3 to about 10 (preferably, 3 to about 7) for each $(C_sH_{2s}O)$, t is an integer of 1 to about 6 (preferably, 1 to about 3; more preferably, 1 to 2), and r' is an integer of 1 to about 10 (preferably, 1 to about 5; more preferably, 1); with the proviso that the compounds do not exhibit at least one tilted smectic mesophase. Preferably, $R_h$ has from about 4 to about 14 carbon atoms (more preferably from about 4 to about 10).

Such preferred compounds, in general, have enhanced smectic mesophases and low cone tilt angles (relative to the corresponding compounds which do not contain an extended hydrocarbon ether group adjacent to a terminal fluoroalkyl or fluoroether group) making them useful alone, as well as in admixture with other liquid crystal compounds (as dopants or as the major components), for electrooptical display applications. Mixtures of the compounds with other liquid crystal materials can be formulated to provide desired transition temperatures, broad mesophase temperature ranges, and reduced cone tilt angles.

The fluorine-containing liquid crystal compounds useful in carrying out the process of the invention can be prepared by a process comprising the steps of (a) mixing at least one compound represented by the formula

with at least one compound represented by the formula

or mixing at least one compound represented by the formula

with at least one compound represented by the formula

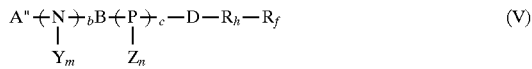

where M, N, P, a, b, c, A, B, X, Y, Z, l, m, n, D, R, $R_h'$, and $R_f$ are as defined above for formula I; and each A', A", B', and B" are independently selected from the group consisting of —H, —Cl, —Br, —I, —OH, —COOH, —CH($CH_2OH$)$_2$, —SH, —SeH, —TeH, —$NH_2$, —COCl, —CHO, —$OSO_2R_f''$, —$OSO_2CH_3$, —NH(C=O)O$C_qH_{2q+1}$, —NCO, —$OSO_2$-cyclo ($C_6H_4$)—$CH_3$, —$CH_2COOH$, and —CH(C(O)O—$C_qH_{2q+1}$)$_2$, where $R_f''$ is a perfluoroalkyl group having from 1 to about 10 carbon atoms and q is an integer of 0 to about 20, and with the proviso that A' can enter into an addition or condensation reaction with A" and that B' can enter into an addition or condensation reaction with B";

and (b) allowing compounds II and III or compounds IV and V to react, optionally in the presence of suitable coupling agent(s), i.e., reagent(s) which effect coupling.

Liquid crystal compositions suitable for use (as composition(s) (b)) in admixture with the above-described liquid crystal compositions (i.e., composition(s) (a)) are those liquid crystal compositions which comprise at least one smectic or latent smectic liquid crystal compound. At least one of compositions (a) and (b) generally must possess optical activity in order for the resulting combination to exhibit a measurable cone tilt angle in a surface-stabilized ferroelectric liquid crystal device. Especially suitable compounds for use in composition(s) (b) are fluorine-containing, smectic or latent smectic liquid crystal compounds (preferably compounds having fluorinated terminal portions such as those compounds described, for example, in U.S. Pat. Nos. 4,886,619 (Janulis), 5,082,587 (Janulis), 5,262,082 (Janulis et al.), 5,399,291 (Janulis et al.), and 5,437,812 (Janulis et al.) and in U.S.S.N. 08/338,957 (Janulis et al.) and U.S.S.N. 08/338,961 (Janulis et al.), the descriptions of which are incorporated herein by reference, as well as compounds having at least one chiral, fluorinated terminal portion).

The process of the invention can be carried out by combining composition(s) (a) and composition(s) (b). The combining or mixing of the compositions can be effected by introducing the compositions to a vessel, generally with simultaneous and/or subsequent agitation or stirring, e.g., roller mixing. The vessel can be either an open or a closed vessel of a size which is sufficient to hold both compositions while allowing room for mixing. The compositions can be formed prior to combination with each other, or, alternatively, one or more of the components of either can be combined with one or more of the components of the other prior to addition of the remaining components. Any order and manner of combination of the components of the compositions is acceptable. The resulting combination is preferably agitated or stirred sufficiently that a homogeneous mixture is achieved. This is preferably facilitated by applying sufficient heat to melt the combination or by dissolving the combination in a solvent, e.g., a polar aprotic solvent, with subsequent solvent removal, e.g., by evaporation.

The liquid crystal compounds to be utilized in the process can be selected based upon the magnitudes of their cone tilt angles (or, in the case of latent smectic liquid crystal compounds, the magnitudes of the cone tilt angle of mixtures containing the latent compound(s)), which can be determined by using a polarizing microscope equipped with a hot stage, as described below in the Examples. In general, composition (b) (generally having a greater cone tilt angle) can be combined with composition (a) (generally having a smaller cone tilt angle) to obtain a combination having a desired intermediate cone tilt angle. Preferably, composition (s) (a) are utilized in amount(s) such that the resulting combination has a cone tilt angle between about 10 and about 35 degrees (more preferably, between about 18 and about 26 degrees; most preferably, between about 18 and about 23 degrees). However, in some cases a cone tilt angle outside of these ranges may be desirable for a particular purpose and can be achieved by the mixing of compositions (a) and (b). Net cone tilt angles within these ranges can generally be achieved through an iterative process of combining compositions (a) and (b) in varying ratios and measuring the net cone tilt angles of the resulting combinations.

Objects and advantages of this invention are further illustrated by the following examples, but the particular materials and amounts thereof recited in these examples, as well as other conditions and details, should not be construed to unduly limit this invention.

In the following examples, all temperatures are in degrees Celsius and all parts and percentages are by weight unless indicated otherwise. Commercially available materials were chemically transformed by reaction pathways well-known to those skilled in the art and detailed in the examples. Chemical transformations were comprised of acylation, esterification, etherification, alkylation, and combinations thereof using fluorine-containing and non-fluorine-containing reactants to provide the precursor compounds, which, in turn, were allowed to react together to yield the fluorine-containing liquid crystal compounds used in the process of the invention.

Liquid crystal compounds prepared as described below were characterized by their melting or boiling points, and their structures were confirmed using at least one of the following methods of analysis: high pressure liquid chromatography (HPLC); $^{13}C$, $^{1}H$, and $^{19}F$ nuclear magnetic resonance (NMR) ; and infrared and mass spectroscopies.

EXAMPLES

The 5-alkyl-2-(4-hydroxyphenyl) pyrimidines used in the examples were prepared essentially as described by Zaschke and Stolle in "Synthese niedrigschmelzender KristalLin-Flussiger Heterocyclen; 5-n-Alkyl-2-[4-n-alkanoyloxy-phenyl]pyrimidine," Z.Chem. 15, 441–3 (1975). (S)- and (R)-2-fluoro-decyl- p-toluenesulfonate were prepared essentially as described by Nohira et al. in Mol. Cryst. Liq. Cryst. 180B, 379 (1990). Fluorina-ed alcohols were prepared essentially as described in U.S. Pat. No. 5,262,082 (Janulis et al.; the description of which is incorporated herein by reference) by sodium borohydride reduction of the corresponding perfluorinated acids (or derivatives), which had been prepared by electrochemical fluorination (ECF) or by direct fluorination (using elemental fluorine) of the corresponding hydrocarbon acids (or derivatives). See, e.g., the description of ECE given in U.S. Pat. No. 2,519,983 (Simons), the description of which is incorporated herein by reference. Direct fluorination is described, e.g., in U.S. Pat. No. 5,362,919 (Costello et al.), the description of which is also incorporated herein by reference.

Examples 1–28 describe procedures for preparing liquid crystal compounds of the invention, which can be used in the process of the invention. The chemical structure of each compound is given in Table 1.

EXAMPLE 1

Preparation of 5-Octyl-2-[4-(5-(2-(2-(2- (trifluoromethoxy) tetrafluoroethoxy)tetrafluoroethoxy) -2,2-difluoroethoxy) pentyl)-phenyl]pyrimidine

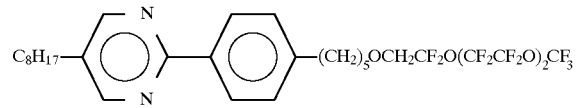

The starting material, 5 -(trifluoromethoxy) tetrafluoroethoxy)tetrafluoroethoxy) -2,2-difluoroethoxy) pent-l-ene was prepared by combining 6-bromopentene (85 g, 0.54 mol), (trifluoromethoxy)tetrafluoroethoxy) tetrafluoroethoxy) -2,2-difluoroethanol (115 g, 0.29 mol), Adogen 464™ mixture of $C_9$–$C_{12}$ tetraalkylammonium chlorides (6 g) , and tetrahydrofuran (30 mL). The resulting mixture was heated to 70° C., and potassium hydroxide (30 g, 0.38 mol, in 30 mL water) was slowly added while maintaining the temperature of the mixture below 90° C. On complete addition of the potassium hydroxide, the resulting mixture was stirred at 70–80° C. for two hours, cooled, and water (150 mL) added. The two resulting phases were separated, and the product was isolated by distillation (B.P. 63–67° C. at 5 torr; yield of 116 g)

A 250 mL flask was charged with 9 -borabicyclo[3.3.1] nonane (9-BBN, 1.9 g, 15.7 mmol) and dioxane (30 mL) and cooled to 5° C. 1-(2-(2-(2 -(trifluoromethoxy) tetrafluoroethoxy)tetrafluoroethoxy) -2,2-difluoroethoxy) pent-5-ene (6.0 g, 14.9 mmol, prepared from 1-bromopent-5-ene and 2-(2-(2 -(trifluoromethoxy)tetrafluoroethoxy) tetrafluoroethoxy) -2,2-difluoroethanol) was added to the flask, and the resulting mixture was allowed to stir at room temperature for four hours. 5-octyl-2-(4 -(trifluoromethylsulfonyl)phenyl)pyrimidine (6.03 g, 14.9 mmol), potassium phosphate ( 6.65 g, 31.3 mmol), and dimethyl formamide (30 mL) were added to the mixture, followed by a nitrogen purge. $PdCl_2(dppf)$ (approximately 3 mole %) was then added, and the resulting mixture was heated to 100° C. for 16 hours.

The mixture was quenched with water and then extracted with toluene. The combined toluene extracts were chromatographed on silica eluting with toluene, followed by a second chromatography, eluting with 10:1 (volume) heptane/ethyl acetate. The product was further purified by recrystallization from heptane followed by Kugelrohr distillation (190° C. at 0.01 torr) to provide a yield of 4.1 g.

EXAMPLE 2

Preparation of 5-Octyl-2-[4-(3-(2-(2-(2 -(trifluoromethoxy) tetrafluoroethoxy)tetrafluoroethoxy) -2,2-difluoroethoxy) propyl)-phenyl]pyrimidine

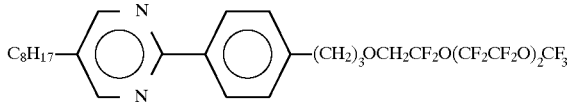

The title compound was prepared essentially as in Example 1 by combining 3-(2-(2-(2 -(trifluoromethoxy) tetrafluoroethoxy)tetrafluoroethoxy) -2,2-difluoroethoxy) prop-1-ene (6.49 g, 16.0 mmol, prepared from 1-bromopropene and 2-(2-(2 -(trifluoromethoxy) tetrafluoroethoxy)tetrafluoroethoxy) -2,2-difluoroethanol) and 5-octyl-2-(4 -(trifluoromethylsulfonyl)phenyl) pyrimidine (6.03 g, 14.9 mmol). The resulting mixture was quenched with water, and the crude product: was isolated by extraction with toluene and further purified essentially as in Example 1 to provide a yield of 4.4 g.

EXAMPLE 3

Preparation of 5-Octyl-2-(5-(2-(2 -(pentafluoroethoxy) tetrafluoroethoxy)-2,2 -difluoroethoxy)pentyl)phenyl) pyrimidine

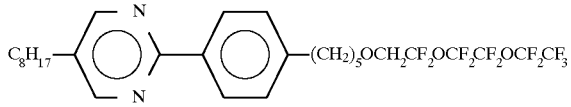

The title compound was prepared essentially as in Example 1 by combining 5-(2-(2 -(pentafluoroethoxy) tetrafluoroethoxy)-2,2 -difluoroethoxy)pent-1-ene (6.0 g, 15.0 mmol, prepared from 1-bromopent-5-ene and 2-(2 -(pentafluoroethoxy)tetrafluoroethoxy)-2,2 -difluoroethanol) and 5-octyk-2-(4 -(trifluoromethylsulfonyl)phenyl)pyrimidine (6.0 g, 14.9 mmol). The resulting mixture was quenched with water, and the crude product was isolated by extraction with toluene and further purified essentially as in Example 1 to provide a yield of 4.5 g.

EXAMPLE 4

Preparation of 5-Octyl-2-[4-(3-(2-(2 -(pentafluoroethoxy) tetrafluoroethoxy)-2,2 -difluoroethoxy)propyl)phenyl] pyrimidine

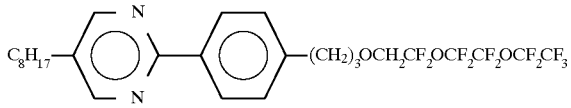

The title compound was prepared essentially as in Example 1 by combining 3-(2-(2 -(pentafluoroethoxy) tetrafluoroethoxy)-2,2 -difluoroethoxy)prop-1-ene (6).O g, 16.1 m=ol, prepared from 1-bromopropene and 2-(2 -(pentafluoroethoxy)tetrafluoroethoxy)-2,2 -difluoroethanol) and 5-octy2.-2-(4 -(trifluoromethylsulfonyl)phenyl)pyrimidine (6.5 g, 16.1 mmol). The resulting mixture was quenched with water, and the crude product was isolated by extraction with toluene and further purified essentially as in Example 1 to provide a yield of 6.49 g.

EXAMPLE 5

Preparation of 5-Octyl-2-[4-(3-(2 -(nonafluorobutoxy) -2,2, 3,3-tetrafluoropropoxy)-propyl)phenyl]pyrimidine

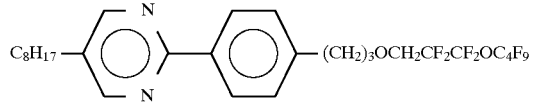

The title compound was prepared essentially as in Example 1 by combining 3-(2-(nonafluorobutoxy) -2,2-difluoroethoxy)prop-1-ene (6.0 g, 14.8 mmol, prepared from 1-bromopropene. and 2-(nonafluorobutoxy) -2,2,3,3-tetrafluoropropanol) and 5-octyl-2-(4 -(trifluoromethylsulfonyl)phenyl)pyrimidine (5.9 g, 14.8 mmol). The resulting mixture was quenched with water, and the crude product was isolated by extraction with toluene and further purified essentially as in Example 1 to provide a yield of 5.96 g.

EXAMPLE 6

Preparation of 5-Octyl-2-[4-(3-(2-(2 -(trifluoromethoxy) tetrafluoroethoxy)-2,2 -difluoroethoxy)propyl)phenyl] pyrimidine

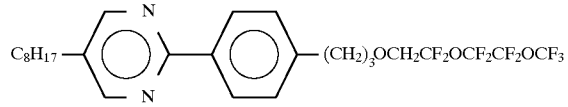

The title compound was prepared essentially as in Example 1 by combining 3-(2-(2 -(trifluoromethoxy) tetrafluoroethoxy)-2,2 -difluoroethoxy)-prop-l-ene (6.0 g, 18.6 mmol, prepared from 1-bromopropene and 2-(2 -(trifluoromethoxy)tetrafluoroethoxy)-2,2 -difluoroethanol) and 5-octyl-2-(4 -(trifluoromethylsulfonyl)phenyl) pyrimidine (7.5 g, 18.6 mmol). The resulting mixture was quenched with water, and the crude product was isolated by extraction with toluene and further purified essentially as in Example 1 to provide a yield of 7.2 g.

EXAMPLE 7

Preparation of 5-Octyl-2-[4-(6-(2-(2 -(nonafluorobutoxy) tetrafluoroethoxy)-2,2 -difluoroethoxy)hexyl)phenyl] pyrimidine

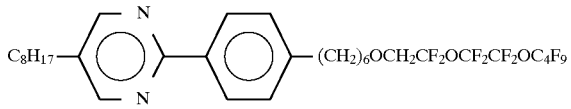

The title compound was prepared essentially as in Example 1 by combining 6-(2-(2 -(nonafluorobutoxy) tetrafluoroethoxy)-2,2 -difluoroethoxy)hex-1-ene (6.0 g, 11.7 mmol, prepared from 1-bromohex-5-ene and 2-(2 -(nonafluorobutoxy)tetrafluoroethoxy)-2,2 -difluoroethanol) and 5-octyl-2-(4 -(trifluoromethylsulfonyl)phenyl) pyrimidine (4.7 g, 11.7 mmol). The resulting mixture was quenched with water, and the crude product was isolated by extraction with toluene and further purified essentially as in Example 1 to provide a yield of 4.45g.

EXAMPLE 8

Preparation of 5-Hexyl-2-[4-(6-(2-(2-(nonafluorobutoxy)tetrafluoroethoxy)-2,2-difluoroethoxy)hexyl)phenyl]pyrimidine

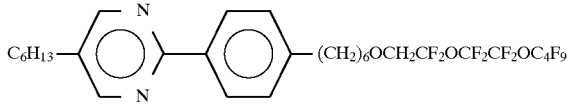

The title compound was prepared essentially as in Example 1 by combining 6-(2-(2-(nonafluorobutoxy)tetrafluoroethoxy)-2,2-difluoroethoxy)hex-1-ene (6.0 g, 11.7 mmol) and 5-hexyl-2-(4-(trifluoromethylsulfonyl)phenyl)pyrimidine (4.4 g, 11.7 mmol). The resulting mixture was quenched with water, and the crude product was isolated by extraction with toluene and further purified essentially as in Example 1 to provide a yield of 4.89 g.

EXAMPLE 9

Preparation of 5-Octyl-2-[4-(4-(2-(2-(2-(trifluoromethoxy)tetrafluoroethoxy)tetrafluoroethoxy)-2,2-difluoroethoxy)butyl)phenyl]pyrimidine

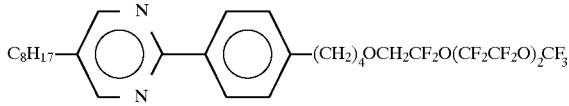

The title compound was prepared essentially as in Example 1 by combining 4-(2-(2-(2-(trifluoromethoxy)tetrafluoroethoxy)tetrafluoroethoxy)-2,2-difluoroethoxy)-but-1-ene (4.2 g, 9.3 mmol, prepared from dibromobutane and 2-(2-(2-(trifluoromethoxy)tetrafluoroethoxy)tetrafluoroethoxy)-2,2-difluoroethanol, followed by dehydrohalogenation) and 5-octyl-2-(4-(trifluoromethylsulfonyl)phenyl)pyrimidine (3.76 g, 9.3 mmol). The resulting mixture was quenched with water, and the crude product was isolated by extraction with toluene and further purified essentially as in Example 1 to provide a yield of 3.58 g.

EXAMPLE 10

Preparation of 5-Octyl-2-[4-(6-(2-(2-(trifluoromethoxy)tetrafluoroethoxy)-2,2-difluoroethoxy)hexyl)phenyl]pyrimidine

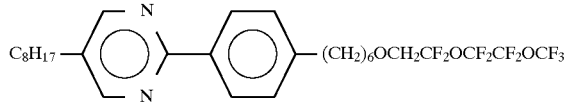

The title compound was prepared essentially as in Example 1 by combining 6-(2-(2-(trifluoromethoxy)tetrafluoroethoxy)-2,2-difluoroethoxy)hex-1-ene (6.0 g, 14.9 mmol, prepared from 1-bromohex-5-ene and 2-(2-(trifluoromethoxy)tetrafluoroethoxy)-2,2-difluoroethanol) and 5-octyl-2-(4-(trifluoromethylsulfonyl)phenyl)pyrimidine (6.0 g, 14.9 mmol). The resulting mixture was quenched with water, and the crude product was isolated by extraction with toluene and further purified essentially as in Example 1 to provide a yield of 5.25 g.

EXAMPLE 11

Preparation of 5-Decyl-2-[4-(6-(2-(2-(nonafluorobutoxy)tetrafluoroethoxy)-2,2-difluoroethoxy)hexyl)phenyl]pyrimidine

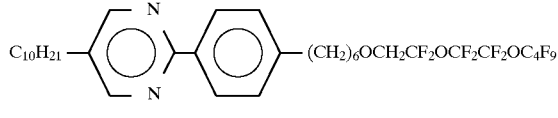

The title compound was prepared essentially as in Example 1 by combining 6-(2-(2-(nonafluorobutoxy)tetrafluoroethoxy)-2,2-difluoroethoxy)hex-1-ene (6.0 g, 11.7 mmol) and 5-decyl-2-(4-(trifluoromethylsulfonyl)phenyl)pyrimidine (5.0 g, 11.7 mmol). The resulting mixture was quenched with water, and the crude product was isolated by extraction with toluene and further purified essentially as in Example 1 to provide a yield of 5.8 g.

EXAMPLE 12

Preparation of 5-Octyl-2-[4-(6-(4-(pentafluoroethoxy)-2,2,3,3,4,4-hexafluorobutoxy)hexyl)phenyl]pyrimidine

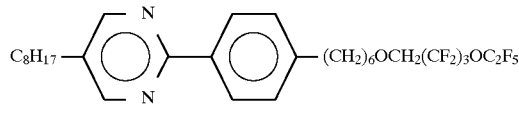

The title compound was prepared essentially as in Example 1 by combining 6-(4-(pentafluoroethoxy)-2,2,3,3,4,4-hexafluorobutoxy)-hex-1-ene (6.0 g, 15.1 mmol, prepared from 1-bromohex-5-ene and 4-(pentafluoroethoxy)-2,2,3,3,4,4-hexafluorobutanol) and 5-octyl-2-(4-(trifluoromethylsulfonyl)phenyl)pyrimidine (6.1 g, 15.7 mmol). The resulting mixture was quenched with water, and the crude product was isolated by extraction with toluene and further purified essentially as in Example 1 to provide a yield of 4.14

EXAMPLE 13

Preparation of 5-Octyl-2-[4-(6-(2-(2-(2-(trifluoromethoxy)tetrafluoroethoxy)tetrafluoroethoxy)-2,2-difluoroethoxy)hexyl)phenyl]pyrimidine

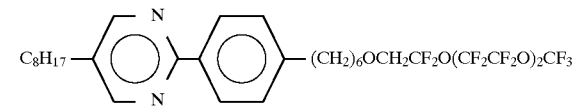

The title compound was prepared essentially as in Example 1 by combining 6-(2-(2-(2-(trifluoromethoxy)tetrafluoroethoxy)tetrafluoroethoxy)-2,2-difluoroethoxy)hex-1-ene (6.0 g, 12.5 mmol) and 5-octyl-2-(4-(trifluoromethylsulfonyl)phenyl)pyrimidine (5.05 g, 12.5 mmol). The resulting mixture was quenched with water, and the crude product was isolated by extraction with toluene and further purified essentially as in Example 1 to provide a yield of 5.2

EXAMPLE 14

Preparation of 5-Octyl-2-[4-(6-(4-(heptafluoropropoxy)-2,2,3,3,4,4-hexafluorobutoxy)hexyl)phenyl]pyrimidine

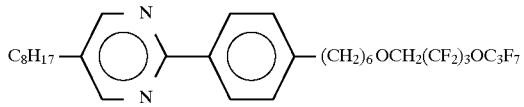

The title compound was prepared essentially as in Example 1 by combining 6-(4-(heptafluoropropoxy) -2,2,3,3,4,4-hexafluorobutoxy)hex-1-ene (6.0 g, 13.4 mmol, prepared from 1-bromohex-5-ene and 4 -(heptafluoropropoxy) -2,2,3,3,4,4-hexafluorobutanol) and 5-octyl-2-(4-(trifluoromethylsulfonyl)phenyl)pyrimidine (5.4 g, 13.4 mmol). The resulting mixture was quenched with water, and the crude product was isolated by extraction with toluene and further purified essentially as in Example 1 to provide a yield of 5.6 g.

EXAMPLE 15
Preparation of 5-Octyl-2-[4-(6-(4 -(nonafluorobutoxy) -2,2,3,3,4,4-hexafluorobutoxy)hexyl)phenyl]pyrimidine

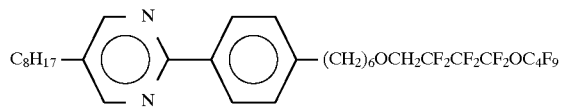

The title compound was prepared essentially as in Example 1 by combining 6-(4-(nonafluorobutoxy) -2,2,3,3,4,4-hexafluorobutoxy)hex-1-ene (6.0 g, 16.0 mmol, prepared from 1-bromohex-5-ene and 4 -(nonafluorobutoxy)-2,2,3,3,4,4-hexafluorobutanol) and 5-octyl-2-(4-(trifluoromethylsulfonyl)phenyl)pyrimidine (4.87 g, 16.0 mmol). The resulting mixture was quenched with water, and the. crude product was isolated by extraction with toluene and further purified essentially as in Example 1 followed by Kugelrohr distillation (187°-92° C. at 0.01 to 0.015 torr) to provide a yield of 4.89 g.

EXAMPLE 16
Preparation of 5-Octyl-2-[4-(6-(2-(2 -(trifluoromethoxy) tetrafluoroethoxy) -2,2,3,3,4,4,5,5,6,6— decafluorohexyloxy)hexyl)phenyl]pyrimidine

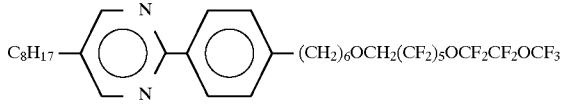

The title compound was prepared essentially as in Example 1 by combining 6-(2-(2 -(trifluoromethoxy) tetrafluoroethoxy) -2,2,3,3,4,4,5,5,6,6— decafluorohexyloxy)hex-1-ene (6.0 g, 11.0 mmol, prepared from 1-bromohex-5-ene and 2-(2 -(trifluoromethoxy) tetrafluoroethoxy) -2,2,3,3,4,4,5,5,6,6—decafluorohexanol) and 5-octyl-2 -(4-(trifluoromethylsulfonyl)phenyl) pyrimidine (4.30 g, 11.0 mmol). The resulting mixture was quenched with water, and the crude product was isolated by extraction with toluene and further purified essentially as in Example 1 followed by Kugelrohr distillation (187° -92° C. at 0.015 torr) to provide a yield of 5.78 g.

EXAMPLE 17
Preparation of 5-Hexyl-2-[4-(6-(2-(2-(2 -(trifluoromethoxy) tetrafluoroethoxy)tetrafluoroethoxy) -2,2-difluoroethoxy) hexyl)phenyl]pyrimidine

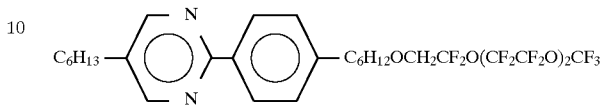

The title compound was prepared essentially as in Example 1 by combining 6-(2-(2-(2 -(trifluoromethoxy) tetrafluoroethoxy)tetrafluoroethoxy) -2,2-difluoroethoxy) hex-1-ene (6.0 g, 12.4 mmol) and 5 -hexyl-2-(4-(trifluoromethylsulfonyl)phenyl)pyrimidine (4.70 g, 12.4 mmol). The resulting mixture was quenched with water, and the crude product was isolated by extraction with toluene and further purified essentially as in Example 1 followed by Kugelrohr distillation (187-92° C. at 0.31 to 0.015 torr) to provide a yield of 4.45 g.

EXAMPLE 18
Preparation of 5-Decyl-2-[4-(6-(4 -(pentafluoroethoxy) -2,2,3,3,4,4-hexafluorobutoxy)hexyl)phenyl]pyrimidine

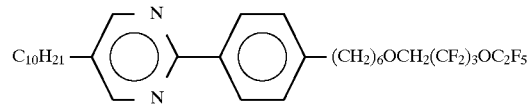

The title compound was prepared essentially as in Example 1 by combining 6-(4-(pentafluoroethoxy) -2,2,3,3,4,4-hexafluorobutoxy)hex-1-ene (6.0 g, 15.0 mmol, prepared from 1-bromohex-5-ene and 4 -(pentafluoroethoxy)-2,2,3,3,4,4-hexafluorobutanol) and 5-decyl-2-(4-(trifluoromethylsulfonyl)phenyl)pyrimidine (6.52 g, 15.0 mmol). The resulting mixture was quenched with water, and the crude product was isolated by extraction with toluene and further purified essentially as in Example 1 followed by Kugelrohr distillation (187-92° C. at 0.01 to 0.015 torr) to provide a yield of 5.68 g.

EXAMPLE 19
Preparation of 5-Octyl-2-[4-(5-(2-(2 -(nonafluorobutoxy) tetrafluoroethoxy)-2,2 -difluoroethoxy)pent-1-ynyl)phenyl) pyrimidine

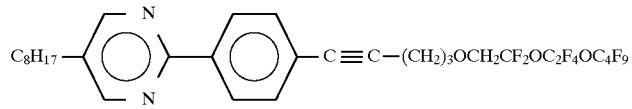

The title compound was prepared by combining 5-octyl-2-(4-(trifluoromethylsulfonyl)phenyl)pyrimidine (2.04 g, 4.8 mmol), 5-(2-(2 -(nonafluorobutoxy)tetrafluoroethoxy) -2,2 -difluoroethoxy)pent-1-yne (3.0 g, 6 mmol, prepared from 1-bromopent-4-yne and 2-(2 -(nonafluorobutoxy) tetrafluoroethoxy)-2,2 -difluoroethanol), and $PdCl_2(PPh_3)_2$ (0.12 g) in triethylamine (6 mL) and dimethylformamide (6 mL). The resulting mixture was heated at 80° C. for ten hours, was quenched with water, and was extracted with methylene chloride. The combined organic solution was washed with water and dried. After evaporation of the solvent, the crude product was further purified by chromatography (eluting with 20:1 (volume) hexane/ethyl acetate), recrystallization from hexane, and Kugelrohr distillation (230° C. at 0.8 torr) to provide 2.38 g.

EXAMPLE 20

Preparation of 5-Decyl-2-[4-(5-(2-(2 -(nonafluorobutoxy) tetrafluoroethoxy)-2,2 -difluoroethoxy)pent-1-ynyl)phenyl] pyrimidine

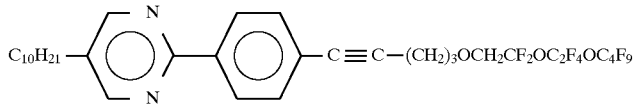

The title compound was prepared essentially as in Example 19 by combining 5-decyl-2-[4 -(trifluoromethylsulfonyl)phenyl]pyrimidine (1.0 g, 2.3 mmol), 5-(2-(2-(nonafluorobutoxy)tetrafluoroethoxy) -2,2-difluoroethoxy)pent-1-yne (2.16 g, 4.3 mmol), and $PdCl_2$ $(PPh_3)_2$(0.17 g) in triethylamine (4 mL) and dimethylformamide (2 mL). The resulting mixture was heated at 100° C. for four hours, was hydrolyzed, and then the crude product was further purified by chromatography and recrystallization from ethanol followed by Kugelrohr distillation to provide 0.73 g.

EXAMPLE 21

Preparation of 5-Hexyloxy-2-[4-(5-(2-(2 -(nonafluorobutoxy)tetrafluoroethoxy)-2,2 - 2difluoroethoxy)pent-1-ynyl)phenyl]pyrimidine

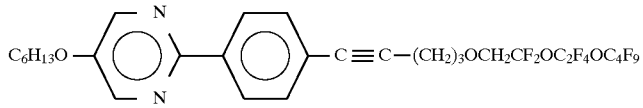

The title compound was prepared essentially as in Example 19 by combining 5-hexyloxy-2-(4 -(trifluoromethylsulfonyl)phe2nyl)pyrimidine (2.0 g, 5.1 mmol), 5-(2-(2-(nonafluorobutoxy)tetrafluoroethoxy) -2,2-difluoroethoxy)pent-1-yne (3.1 g, 6.2 mmol), and $PdCl_2$ $(PPh_3)_2$(0.13 g) in triethylamine (4 mL) and dimethylformamide (5 mL). The resulting mixture was heated at 80° C. for four hours, hydrolyzed, extracted into $CH_2Cl_2$, washed with water, and the solvent evaporated. The crude product was further purified by chromatography, followed by Kugelrohr distillation to provide 1.9 g.

EXAMPLE 22

Preparation of 5-Octyl-2-[4-(3-(2-(2 -(nonafluorobutoxy) tetrafluoroethoxy)-2,2 -difluoroethoxy)propyl)phenyl] pyrimidine

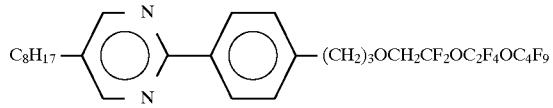

The title compound was prepared essentially as in Example 1 by combining 3-(2-(2 -(nonafluorobutoxy) tetrafluoroethoxy)-2,2 -difluoroethoxy)pro-1-ene (5.6 g, 12.0 mmol) and 5 -octyl-2-(4-(trifluoromethylsulfonyl) phenyl)pyrimidine (4.87 g, 12.0 mmol) and 9-borabicyclo [3.3.1] nonane (26 mmol in THF) in dioxane (30 mL). After stirring overnight at room temperature, $PdCl_2$ (dppf) (0.1 g) was added, and the resulting mixture was stirred at 90°-5° C. The mixture was then quenched with aqueous HCl, and the crude product was isolated by extraction with $CH_2Cl_2$ and was further purified essentially as in Example 1 to provide a yield of 4.4 g.

EXAMPLE 23

Preparation of 5-Decyl-2-[4-(3-(2-(2 -(nonafluorobutoxy) tetrafluoroethoxy)-2,2 -difluoroethoxy)propyl)phenyl] pyrimidine

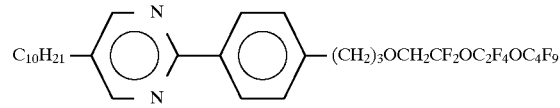

The title compound was prepared essentially as in Example 1 by combining 3-(2-(2 -(nonafluorobutoxy) tetrafluoroethoxy)-2,2 -difluoroethoxy)prop-l-ene (5.6 g, 12.0 mmol) and 5 -decyl-2-(4-(trifluoromethylsulfonyl) phenyl)pyrimidine (5.2 g, 12.0 mmol) and 9-borabicyclo [3.3.1] nonane (25.3 mmol in THF) in tetrahydrofuran (30 mL). After stirring overnight, $PdCl_2$(dppf) (0.1 g) was added, and the resulting mixture was stirred at 80°–90° C. for another 24 hours. The mixture was then quenched with aqueous HCl, and the crude product was isolated by extraction with $CH_2Cl_2$ and was further purified essentially as in Example 1 to provide a yield of 3.88 g.

EXAMPLE 24

Preparation of 5-Heptyloxy-2-[4-(3-(2-(2 -(nonafluorobutoxy)tetrafluoroethoxy)-2,2 -difluoroethoxy) propyl)phenyl]pyrimidine

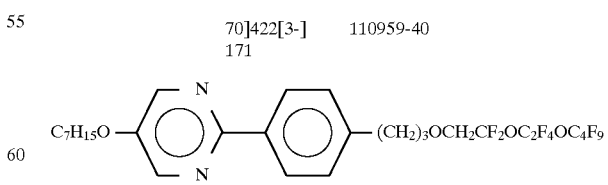

The title compound was prepared essentially as in Example 1 by combining 3-(2-(2 -(nonafluorobutoxy) tetrafluoroethoxy)-2,2 -difluoroethoxy)prop-l-ene (5.0 g, 10.6 mmol) and 5 -heptyloxy-2-(4 -(trifluoromethylsulfonyl)phenyl)pyrimidine (3.1 g, 7.7 mmol) and 9-borabicyclo[3.3.1]nonane (7.5 mmol in THF) in tetrahydrofuran (30 mL). After stirring overnight, PdCl$_2$ (dppf) (0.1 g) was added, and the resulting mixture was stirred at 95° C. for another 8 hours. The mixture was then quenched with aqueous HCl, and the crude product was isolated by extraction with CH$_2$Cl$_2$ and was further purified essentially as in Example 1 to provide a yield of 2.8 g.

Example 25
Preparation of 5-Hexyloxy-2[4—(3-(2-(2-(nonafluorobutoxy)tetrafluoroethoxy)-2,2-difluoroethoxy)propyl)phenyl]pyrimidine

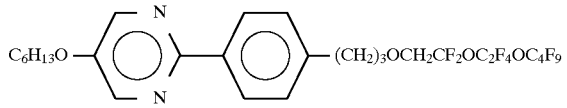

The title compound was prepared essentially as in Example 1 by combining 3-(2-(2-(nonafluorobutoxy)tetrafluoroethoxy)-2,2-difluoroethoxy)prop-l-ene (3.0 g, 6.0 mmol) and 5-hexylyoxy-2-(4-(trifluoromethylsulfonyl)phenyl)pyrimidine (1.93 g, 4.7 mmol) and 9-borabicyclo [3.3.1] nonane (6.5 mmol in THF) in dimethylformamide (20 mL). After stirring overnight, PdCl$_2$(dppf) (0.1 g) was added, and the resulting mixture was stirred at 95° C. for another 20 hours. The mixture was then quenched with aqueous HCl, and the crude product was isolated by extraction with CH$_2$Cl$_2$ and was further purified essentially as in Example 1 to provide a yield of 0.89 g.

EXAMPLE 26
Preparation of 5-Hexyloxy-2-[4-(6-(2-(2-(nonafluorobutoxy)tetrafluoroethoxy)-2,2-difluoroethoxy) hexyl)phenyl]pyrimidine

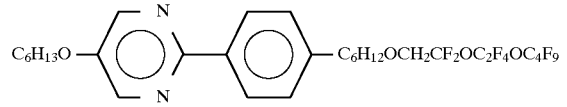

The title compound was prepared essentially as in Example 1 by combining 6-(2-(2-(nonafluorobutoxy) tetrafluoroethoxy)-2,2-difluoroethoxy)hex-1-ene (4.0 g, 7.8 mmol, prepared from 1-bromohex-5-ene and 2-(2-(nonafluorobutoxy)tetrafluoroethoxy)-2,2-difluoroethanol) and 5-hexyloxy-2-(4-(trifluoromethylsulfonyl)phenyl)pyrimidine (3.0 g, 7.8 mmol). The resulting mixture was quenched with water, and the crude product was isolated by extraction with toluene and was further purified essentially as in Example 1.

EXAMPLE 27
Preparation of 5-Heptyloxy-2-(6-(2-(2-(pentafluoroethoxy)tetrafluoroethoxy)-2,2-difluoroethoxy)hexyl)phenyl) pyrimidine

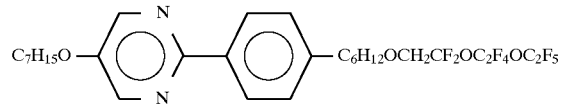

The title compound was prepared essentially as in Example 1 by combining 6-(2-(2-(pentafluoroethoxy) tetrafluoroethoxy)-2,2-difluoroethoxy)hex-1-ene (3.5 g, 8.5 mmol, prepared from 1-bromohex-5-ene and 2-(2-(pentafluoroethoxy)tetrafluoroethoxy)-2,2-difluoroethanol) and 5-heptyloxy-2-(4-(trifluoromethylsulfonyl)phenyl)pyrimidine (3.4 g, 8.5 mmol). The resulting mixture was quenched with water, and the crude product was isolated by extraction with toluene and was further purified essentially as in Example 1

EXAMPLE 28

Preparation of 5-Heptyloxy-2-(4-(2-(2-(pentafluoroethoxy) tetrafluoroethoxy)-2,2-difluoroethoxy)butyl)phenyl) pyrimidine

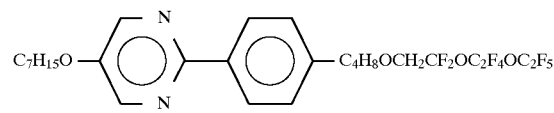

The title compound was prepared essentially as in Example 1 by combining 4-(2-(2-(pentafluoroethoxy) tetrafluoroethoxy)-2,2-difluoroethoxy)but-1-ene (3.0 g, 7.8 mmol, prepared from 1,4-dibromobutane and 2-(2-(pentafluoroethoxy)tetrafluoroethoxy)-2,2-difluoroethanol, followed by dehydrobromination) and 5-octyl-2-(4-(trifluoromethylsulfonyl)phenyl)pyrimidine (3.16 g, 7.8 mmol). The resulting mixture was quenched with water, and the crude product was isolated by extraction with toluene and was further purified essentially as in Example 1 to provide a yield of 0.51 g (B.P. 190° C. at 0.01 torr).

The compounds of Table 1 below were evaluated for transition temperatures by differential scanning calorimetry (DSC) and/or optical observation of material phase changes using a Linkham TMH600 hot stage and a polarizing microscope. The transition temperatures (° C.) were obtained upon cooling through the isotropic state (I) to the smectic A mesophase (S$_A$), the smectic C mesophase (S$_C$), and higher order mesophases (M1 and M2) or the crystalline state (K) and are set forth in the table. Using essentially the method described below for Example 29, cone tilt angle was measured for some of the compounds shown in Table 1 by preparing a mixture of 95 weight percent of a compound of the invention and 5 weight percent 5-octyl-2-[4-((R)-2-fluoro-3-(2-(2-(nonfluorobutoxy)tetrafluoroethoxy)-2,2-difluoroethoxy)propoxy)phenyl]pyrimidine (prepared essentially as described in International Patent Publication No. WO 96/33251, Example 4) as a high polarization additive. The compounds were combined in a small vial at room temperature, and the resulting combination was heated to the isotropic state with manual roller mixing. Cone tilt angle data is often collected at reduced temperatures of −1° C., −5° C., −10° C., −15° C., −20° C., −30° C., −40° C., and −50° C. The cone tilt angle data shown in Table 1 is the maximum angle measured at a reduced temperature near +30° C. to −40° C.

TABLE 1

Mesophase Transition Temperatures (°C.) and Cone Tilt Angles (Degrees)

| Example | Structure | I to $S_A$ | to $S_C$ | to $S_{M2}/K$ | Cone Tilt Angle |
|---|---|---|---|---|---|
| 1 | $C_8H_{17}$–[pyrimidine]–[phenyl]–$(CH_2)_5OCH_2CF_2O(CF_2CF_2O)_2CF_3$ | 91 | — | −18 | |
| 2 | $C_8H_{17}$–[pyrimidine]–[phenyl]–$(CH_2)_3OCH_2CF_2O(CF_2CF_2O)_2CF_3$ | 89 | — | <−25 | |
| 3 | $C_8H_{17}$–[pyrimidine]–[phenyl]–$(CH_2)_5OCH_2CF_2OCF_2CF_2OCF_2CF_3$ | 85 | — | −17 | |
| 4 | $C_8H_{17}$–[pyrimidine]–[phenyl]–$(CH_2)_3OCH_2CF_2OCF_2CF_2OCF_2CF_3$ | 83 | — | −35 | |
| 5 | $C_8H_{17}$–[pyrimidine]–[phenyl]–$(CH_2)_3OCH_2CF_2CF_2OC_4F_9$ | 79 | 30 | <−25 | |
| 6 | $C_8H_{17}$–[pyrimidine]–[phenyl]–$(CH_2)_3OCH_2CF_2OCF_2CF_2OCF_3$ | 77 | — | −37 | |
| 7 | $C_8H_{17}$–[pyrimidine]–[phenyl]–$(CH_2)_6OCH_2CF_2OCF_2CF_2OC_4F_9$ | 78 | 51 | −12 | |
| 8 | $C_6H_{13}$–[pyrimidine]–[phenyl]–$(CH_2)_6OCH_2CF_2OCF_2CF_2OC_4F_9$ | 70 | 19 | −37 | |
| 9 | $C_8H_{17}$–[pyrimidine]–[phenyl]–$(CH_2)_4OCH_2CF_2O(CF_2CF_2O)_2CF_3$ | 73 | 38 | −40 | |
| 10 | $C_8H_{17}$–[pyrimidine]–[phenyl]–$(CH_2)_6OCH_2CF_2OCF_2CF_2OCF_3$ | 66 | 21 | −25 | |
| 11 | $C_{10}H_{21}$–[pyrimidine]–[phenyl]–$(CH_2)_6OCH_2CF_2OCF_2CF_2OC_4F_9$ | 78 | 64 | 14/−6 | |
| 12 | $C_8H_{17}$–[pyrimidine]–[phenyl]–$(CH_2)_6OCH_2(CF_2)_3OC_2F_5$ | 75 | 34 | −30 | |

TABLE 1-continued

Mesophase Transition Temperatures (°C.) and Cone Tilt Angles (Degrees)

| Example | Structure | I to $S_A$ | to $S_C$ | to $S_{M2}/K$ | Cone Tilt Angle |
|---|---|---|---|---|---|
| 13 | C$_8$H$_{17}$—[pyrazine]—[phenyl]—(CH$_2$)$_6$OCH$_2$CF$_2$O(CF$_2$CF$_2$O)$_2$CF$_3$ | 80 | 50 | −28 | |
| 14 | C$_8$H$_{17}$—[pyrazine]—[phenyl]—(CH$_2$)$_6$OCH$_2$(CF$_2$)$_3$OC$_3$F$_7$ | 78 | 41 | −28 | |
| 15 | C$_8$H$_{17}$—[pyrazine]—[phenyl]—(CH$_2$)$_6$OCH$_2$CF$_2$CF$_2$CF$_2$OC$_4$F$_9$ | 81 | 47 | −22 | 20.0 |
| 16 | C$_8$H$_{17}$—[pyrazine]—[phenyl]—(CH$_2$)$_6$OCH$_2$(CF$_2$)$_5$OCF$_2$CF$_2$OCF$_3$ | 93 | 58 | −26 | |
| 17 | C$_6$H$_{13}$—[pyrazine]—[phenyl]—C$_6$H$_{12}$OCH$_2$CF$_2$O(CF$_2$CF$_2$O)$_2$CF$_3$ | 73 | — | −38 | 13.0 |
| 18 | C$_{10}$H$_{21}$—[pyrazine]—[phenyl]—(CH$_2$)$_6$OCH$_2$(CF$_2$)$_3$OC$_2$F$_5$ | 75 | 60 | 18/−7 | 17.5 |
| 19 | C$_8$H$_{17}$—[pyrazine]—[phenyl]—C≡C—(CH$_2$)$_3$OCH$_2$CF$_2$OC$_2$F$_4$OC$_4$F$_9$ | 105 | — | 27/−1 | |
| 20 | C$_{10}$H$_{21}$—[pyrazine]—[phenyl]—C≡C—(CH$_2$)$_3$OCH$_2$CF$_2$OC$_2$F$_4$OC$_4$F$_9$ | 106 | — | <30 | |
| 21 | C$_6$H$_{13}$O—[pyrazine]—[phenyl]—C≡C—(CH$_2$)$_3$OCH$_2$CF$_2$OC$_2$F$_4$OC$_4$F$_9$ | 140 | — | 39 | |
| 22 | C$_8$H$_{17}$—[pyrazine]—[phenyl]—(CH$_2$)$_3$OCH$_2$CF$_2$OC$_2$F$_4$OC$_4$F$_9$ | 79 | 39 | 17 | |
| 23 | C$_{10}$H$_{21}$—[pyrazine]—[phenyl]—(CH$_2$)$_3$OCH$_2$CF$_2$OC$_2$F$_4$OC$_4$F$_9$ | 78 | 39 | 16 | |
| 24 | C$_7$H$_{15}$O—[pyrazine]—[phenyl]—(CH$_2$)$_3$OCH$_2$CF$_2$OC$_2$F$_4$OC$_4$F$_9$ | 121 | 92 | <8 | |

TABLE 1-continued

Mesophase Transition Temperatures (°C.) and Cone Tilt Angles (Degrees)

| Example | Structure | I to $S_A$ | to $S_C$ | to $S_{M2}/K$ | Cone Tilt Angle |
|---|---|---|---|---|---|
| 25 | $C_6H_{13}O$—[pyrimidine]—[phenyl]—$(CH_2)_3OCH_2CF_2OC_2F_4OC_4F_9$ | 123 | 98 | −4 | |
| 26 | $C_6H_{13}O$—[pyrimidine]—[phenyl]—$C_6H_{12}OCH_2CF_2OC_2F_4OC_4F_9$ | 103 | 76 | −28 | 25.5 |
| 27 | $C_7H_{15}O$—[pyrimidine]—[phenyl]—$C_6H_{12}OCH_2CF_2OC_2F_4OC_2F_5$ | 101 | 72 | −15 | |
| 28 | $C_7H_{15}O$—[pyrimidine]—[phenyl]—$C_4H_8OCH_2CF_2OC_2F_4OC_2F_5$ | 96 | 69 | −12 | 22.5 |

The data in Table 1 shows that most of the compounds exhibit smectic mesophases and that many of the compounds exhibit a broad smectic C mesophase, which makes the compounds well-suited for use in liquid crystal display devices. As a result of the breadth of the smectic C mesophase, the compounds are useful in admixture with themselves or with other liquid crystal compounds, even at high concentration. The data also shows that the compounds generally exhibit a low temperature I to $S_A$ transition and a low temperature $S_C$ to $S_{M2}/K$ transition, as well as a low cone tilt angle.

In the following Examples and Comparative Examples, pairs of compounds having analogous structures were prepared and their transition temperature data compared. Each pair consisted of a compound of the invention that had its fluorocarbon terminal portion connected to its central core by a covalent bond and an analogous compound that had its fluorocarbon terminal portion connected to its central core through a C—O bond. In each case, the number of atoms in the fluorocarbon terminal portion was the same. The comparative compounds were prepared as follows:

Comparative Example A
Preparation of 5-Hexyloxy-2-[4-(5-(2-(2-(nonafluorobutoxy)tetrafluoroethoxy)-2,2 -difluoroethoxy)pentyloxy)phenyl]pyrimidine A 500 mL flask was charged with 5-(2-(2 -(nonafluorobutoxy)tetrafluoroethoxy)-2,2 -difluoroethoxy)-1-bromopentane (18.6 g, 32 mmol; prepared from 1,5-dibromopentane and 2-(2 -(nonafluorobutoxy) tetrafluoroethoxy)-2,2 -difluoroethanol), 5-hexyloxy-2-(4 -hydroxyphenyl)pyrimidine (8.0 g, 29.4 mmol), potassium carbonate (5.4 g, 39 mmol), and acetonitrile (200 mL), and the resulting mixture was stirred and refluxed overnight under nitrogen. Toluene (150 mL) and water (150 mL) were added to the refluxed mixture. The resulting toluene layer was collected and residual water removed by distillation using a Dean-Stark apparatus. The toluene layer was then filtered through a pad of silica gel and the toluene removed under reduced pressure. The crude product was further purified by distillation using a Kugelrohr apparatus (b.p. 210°- 25° C. at 0.3 torr)

Comparative Example B
Preparation of 5-Heptyloxy-2-[4-(5-(2-(2 -(tetrafluoroethoxy)tetrafluoroethoxy)-2,2 -difluoroethoxy) pentyloxy)phenyl]pyrimidine Using essentially the procedure of Comparative Example A, the title compound was prepared by combining 5-(2-(2-( tetrafluoroethoxy)tetrafluoroethoxy)-2,2 -difluoroethoxy)-1-bromopentane (7.2 g, 15.0 mmol), 5 -heptyloxy-2-(4-hydroxyphenyl)pyrimidine (3 g, 11.0 mmol), potassium carbonate (1.6 g, 12.7 mmol), and acetonitrile (50 mL). The resulting crude product was isolated and purified essentially as in Comparative Example A to yield 4.95 g.

Comparative Example C
Preparation of 5-Heptyloxy-2-[4-(3-(2-(2 -(tetrafluoroethoxy)tetrafluoroethoxy)-2,2 -difluoroethoxy) propyloxy)phenyl]pyrimidine Using essentially the procedure of Comparative Example A, the title compound was prepared by combining 3-(2-(2-( tetrafluoroethoxy)tetrafluoroethoxy)-2,2 -difluoroethoxy)-1-bromopropane (5.1 g, 38.5 mmol), 5 -heptyloxy-2-(4-hydroxyphenyl)pyrimidine (3 g, 11.0 mmol), potassium carbonate (1.6 g, 12.7 mmol), and acetonitrile (58 mL). The resulting crude product was isolated and purified essentially as in Comparative Example A to yield 5.1 g.

Comparative Example D
Preparation of 5-Decyl-2-[4-(5-(2-(2 -(nonafluorobutoxy) tetrafluoroethoxy)-2,2 -difluoroethoxy)pentyloxy)phenyl] pyrimidine Using essentially the procedure of Comparative Example A, the title compound was prepared by combining 5-(2-(2 -(nonafluorobutoxy)tetrafluoroethoxy)-2,2 -difluoroethoxy)

-1-bromopentane (4.4 g, 7.6 mmol), 5-decyl-2-(4-hydroxyphenyl)pyrimidine (2.0 g, 6.4 mmol), potassium carbonate (0.5 g, 10 mmol), acetonitrile (20 mL), and dimethyl formamide (20 mL). The resulting crude product was isolated and purified essentially as in Comparative Example A to yield 4.98 g.

a useful range. Thus, the compounds of the invention surprisingly exhibit particularly good mesophase transition temperature behavior (as described above).

Example 29 describes a liquid crystal compound mixture of the invention and a liquid crystal display device of the invention used according to the process of the invention.

TABLE 2

Mesophase Transition Temperatures (°C.)

| Example | I to $S_A$ | to $S_C$ | to K |
|---|---|---|---|
| $C_6H_{13}O$—[pyrimidine]—[phenyl]—$OC_5H_{10}OCH_2CF_2OC_2F_4OC_4F_9$ <br> Comparative Example A | 124.0 | 95.0 | −10 |
| $C_6H_{13}O$—[pyrimidine]—[phenyl]—$C_6H_{12}OCH_2CF_2OC_2F_4OC_4F_9$ <br> Example 26 | 103.1 | 76.2 | −27.6 |
| $C_7H_{15}O$—[pyrimidine]—[phenyl]—$OC_5H_{10}OCH_2CF_2OC_2F_4OC_2F_5$ <br> Comparative Example B | 121.0 | 75.1 | 0.3 |
| $C_7H_{15}O$—[pyrimidine]—[phenyl]—$C_6H_{12}OCH_2CF_2OC_2F_4OC_2F_5$ <br> Example 27 | 100.6 | 72.4 | −14.7 |
| $C_7H_{15}O$—[pyrimidine]—[phenyl]—$OC_3H_6OCH_2CF_2OC_2F_4OC_2F_5$ <br> Comparative Example C | 117.6 | 79.9 | −5.8 |
| $C_7H_{15}O$—[pyrimidine]—[phenyl]—$C_4H_8OCH_2CF_2OC_2F_4OC_2F_5$ <br> Example 28 | 95.8 | 69 | −11.8 |
| $C_{10}H_{21}$—[pyrimidine]—[phenyl]—$OC_5H_{10}OCH_2CF_2OC_2F_4OC_4F_9$ <br> Comparative Example D | 96.20 | 66.4 | 1.6 |
| $C_{10}H_{21}$—[pyrimidine]—[phenyl]—$C_6H_{12}OCH_2CF_2OC_2F_4OC_4F_9$ <br> Example 11 | 78.30 | 64.1 | −5.8 |

The data in Table 2 shows that both the I to $S_A$ and the $S_C$ to $S_{M2}$/K transition temperatures are generally lower (the former by about 20° C.) for each compound of the invention relative to its corresponding comparative compound, while generally maintaining the $S_A$ to $S_C$ transition temperature in In the following Example, liquid crystal compounds having high cone tilt angles are mixed with a liquid crystal compound of the invention (having low cone tilt angles or latent low cone tilt angles), in order to demonstrate the ability of the latter compounds to provide mixtures having a reduced cone tilt angle relative to those of the former compounds. In this Example, a mixture is prepared and placed into a glass ferroelectric liquid crystal (FLC) test cell having asymmetric alignment layers composed of, e.g., nylon faced with polysiloxane, essentially as described in U.S. Pat. No. 5,377,033 (Radcliffe), the description of which is incorporated herein by reference. The cell is placed on a microscope equipped with a hot stage and a photodetector/oscilloscope. The smectic A to C transition temperature of the mixture is determined by heating the test cell to the smectic A phase of the mixture without an applied electric field (electrodes shorted), aligning the cell to obtain extinction between crossed polarizers, then slowly cooling and watching for a waveform shift on the oscilloscope. The reduced temperature for each subsequent data point is calculated by subtracting the smectic A to C transition temperature from the hot stage temperature. Then a square wave signal is applied to the cell at a field of 12.5 V/micron, and cone tilt angle data is collected at each reduced temperature by measuring and averaging the angle between "off" states (smectic C extinction) on either side of the smectic A extinction angle. Cone tilt angle data is collected for the mixture at reduced temperatures of −1° C., −5° C., −10° C., −15° C., −20° C., −30° C., −40° C., and −50° C. The mesophases of the mixture are also determined (essentially as described above for individual compounds).

EXAMPLE 29

47.5 weight percent 5-decyl-2-[4-(6-(4-(pentafluoroethoxy)-2,2,3,.3,4,4 -hexafluorobutoxy)hexyl)phenyl]pyrimidine (Example 21), 47.8 weight percent 5-octyloxy-2-[4-(2-(2 -(nonafluorobutoxy)tetrafluoroethoxy)-2,2 -difluoroethoxy)phenyl]pyrimidine (prepared essentially as described in U.S. Pat. No. 5,262,082), and 5.2 weight percent 5-octyl-2-[4-((R)-2-fluoro-3-(2-(2 -(nonfluorobutoxy)tetrafluoroethoxy)-2,2 -difluoroethoxy)propoxy)phenyl]pyrimidine (a high polarization additive prepared essentially as described in International Patent Publication No. WO 96/33251, Example 4) are combined essentially as described above. The resulting mixture has a cone tilt angle smaller than the cone tilt angle of the 5-octyloxy-2-[4-(2-(2 -(nonafluorobutoxy)tetrafluoroethoxy)-2,2 -difluoroethoxy)phenyl]pyrimidine base material.

Various modifications and alterations of this invention will become apparent to those skilled in the art without departing from the scope and spirit of this invention.

We claim:

1. A process for controlling the cone tilt angle of a tilted smectic liquid crystal composition comprising the step of combining (a) at least one liquid crystal composition comprising at least one smectic or latent smectic liquid crystal compound comprising (i) an aliphatic fluorocarbon terminal portion comprising a terminal fluoroalkyl or fluoroether group and an alkylene group having at least two carbon atoms and containing at least one catenary ether oxygen atom, (ii) an aliphatic hydrocarbon terminal portion, and (iii) a central core connecting said terminal portions, wherein said alkylene group of said aliphatic fluorocarbon terminal portion is directly linked to said central core by a moiety selected from the group consisting of a covalent bond, —CH═CH—, and —C≡C—; and (b) at least one liquid crystal composition comprising at least one smectic or latent smectic liquid crystal compound; with the provisos that at least one of said compositions (a) and (b) comprises at least one chiral liquid crystal compound and that said combining of compositions (a) and (b) provides an optically active, tilted chiral smectic liquid crystal composition.

2. The process of claim 1 wherein said composition (a) is utilized in an amount such that the resulting combination has a cone tilt angle between about 10 and about 35 degrees.

3. The process of claim 1 wherein said aliphatic fluorocarbon terminal portion is represented by the formula —D—$R_h$—$R_f$, where $R_h$ is an alkylene group having at least two carbon atoms and containing at least one catenary ether oxygen atom; $R_f$ is fluoroalkyl or fluoroether; and D is a moiety selected from the group consisting of a covalent bond, —CH═CH—, and —C≡C—.

4. The process of claim 3 wherein said $R_f$ is perfluoroalkyl or perfluoroether and contains from 1 to about 20 carbon atoms and said $R_h$ contains from 2 to about 14 carbon atoms.

5. The process of claim 4 wherein said $R_h$ contains from 2 to about 10 carbon atoms.

6. The process of claim 1 wherein said smectic or latent smectic liquid crystal compound of said composition (a) is represented by the general formula I:

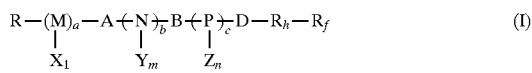

(I)

where M, N, and P are each independently selected from the group consisting of

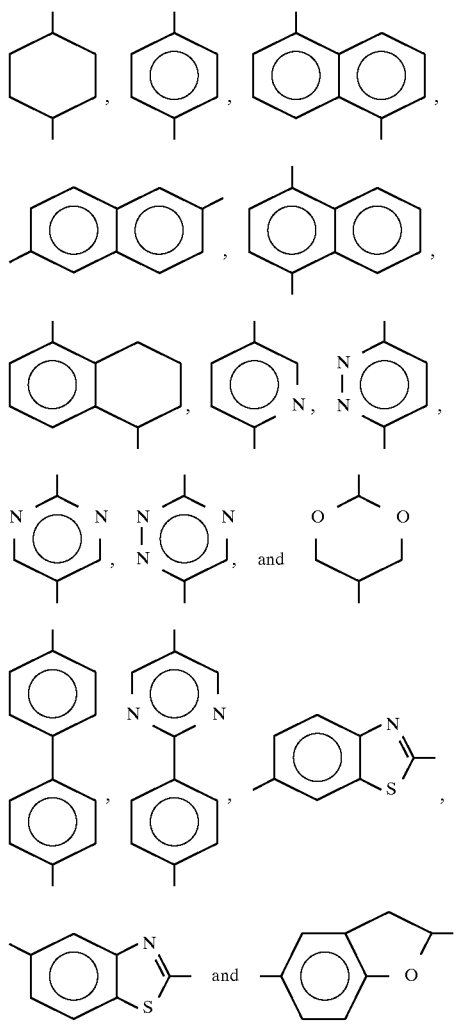

-continued

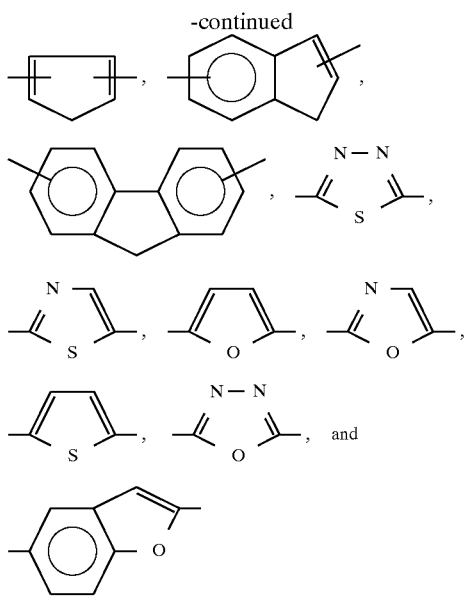

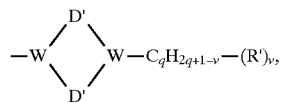

a, b, and c are each independently zero or an integer of from 1 to 3, with the proviso that the sum of a +b +c be at least 1;

each A and B are non-directionally and independently selected from the group consisting of a covalent bond,

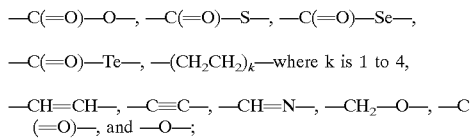

each X, Y, and Z are independently selected from the group consisting of —Cl, —F, —Br, —I, —OH, —OCH$_3$, —CH$_3$, —CF$_3$, —OCF$_3$, —CN, and —NO$_2$;

each 1, m, and n are independently zero or an integer of 1 to 4;

D is a moiety selected from the group consisting of a covalent bond, —CH=CH—, and —C≡C—;

R is selected from the group consisting of

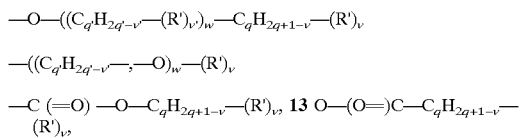

—CR'H—(D') g—CR'H—C$_q$H$_{2q+1-v}$—(R')$_v$, where each R' is independently selected from the group consisting of —Cl, —F, —CF$_3$, —NO$_2$, —CN, —H, —C$_q$H$_{2q+1}$, —O—(O=)C—C$_q$H$_{2q+1}$, —C(=O) =O=C$_q$H$_{2q+1}$, —Br, —OH, and —OC$_q$H$_{2q+1}$; q' is independently an integer of 1 to about 20 for each (C$_{q'}$H$_{2q'}$—O); q is an integer of 1 to about 20; w is an integer of 0 to about 10; v is an integer of 0 to about 6; each v' is independently an integer of 0 to about 6; g is an integer of 1 to about 3; each D' is independently and non-directionally selected from the group consisting of a covalent bond,

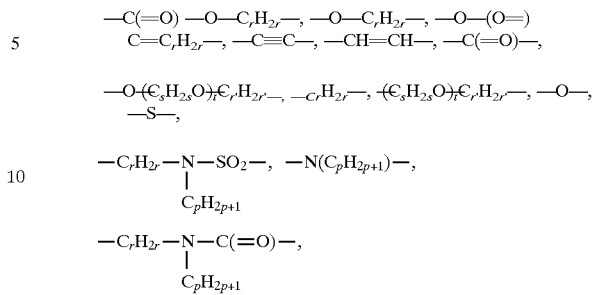

—C$_r$H$_{2r}$—N—SO$_2$—, —N(C$_p$H$_{2p+1}$)—,
         |
         C$_p$H$_{2p+1}$

—C$_r$H$_{2r}$—N—C(=O)—,
         |
         C$_p$H$_{2p+1}$ r and r' are independently integers of 0 to about 20, s is independently an integer of 1 to about 10 for each (C$_s$H$_{2s}$O), t is an integer of ] to about 6, and p is an integer of 0 to about 4, with the proviso that the ring containing D' has from about 3 to about 10 ring atoms; each W is independently selected from the group consisting of N, CR', and SiR';

R$_h$ is an alkylene group having at least two carbon atoms and containing at least one catenary ether oxygen atom; and R$_f$ is fluoroalkyl or fluoroether.

7. The process of claim 6 wherein said R$_f$ is perfluoroalkyl or perfluoroether and contains from 1 to about 20 carbon atoms and said R$_h$ contains from 2 to about 14 carbon atoms.

8. The process of claim 7 wherein said R$_h$ contains from 2 to about 10 carbon atoms.

9. The process of claim 6 wherein said R$_h$ is represented by the general formula (C$_s$H$_{2s}$O)$_t$C$_r$H$_{2r}$—, wherein s is independently an integer of 1 to about 10 for each (C$_s$H$_{2s}$O), t is an integer of 1 to about 6, and r' is an integer of 1 to about 10.

10. The process of claim 9 wherein said s is an integer of about 2 to about 7, said t is an integer of 1 to about 3, and said r' is an integer of 1.

11. The process of claim 6 wherein said R$_f$ is represented by the formula —C$_q$F$_{2q}$X', where q is as defined in claim 6 and X' is hydrogen or fluorine.

12. The process of claim 6 wherein said R$_f$ is represented by the formula —R$_{f'}$—R$_{h'}$, where R$_{f'}$ is a linear or branched, perfluorinated or partially-fluorinated alkylene group having from 1 to about 10 carbon atoms and optionally containing one or more catenary ether oxygen atoms, and R$_{h'}$ is a linear or branched alkyl group having from 1 to about 14 carbon atoms and optionally containing one or more catenary ether oxygen atoms.

13. The process of claim 6 wherein said R$_f$ is represented by the formula —(C$_x$F$_{2x}$O)$_z$C$_y$F$_{2y+1}$, where x is independently an integer of 1 to about 10 for each (C$_x$F$_{2x}$O), y is an integer of 1 to about 10, and z is an integer of 1 to about 10.

14. The process of claim 1 wherein said smectic or latent smectic liquid crystal compound of said composition (b) has at least one fluorinated terminal portion.

15. The process of claim 14 wherein said fluorinated terminal portion comprises at least one perfluoroether group.

16. A mixture of liquid crystal compounds prepared by the process of claim 1, wherein said alkylene group has at least 4 carbon atoms.

17. A liquid crystal display device containing the mixture of claim 16.

18. Fluorine-containing liquid crystal compounds represented by the general formula I:

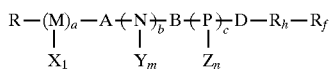 (I)

where M, N, and P are each independently selected from the group consisting of

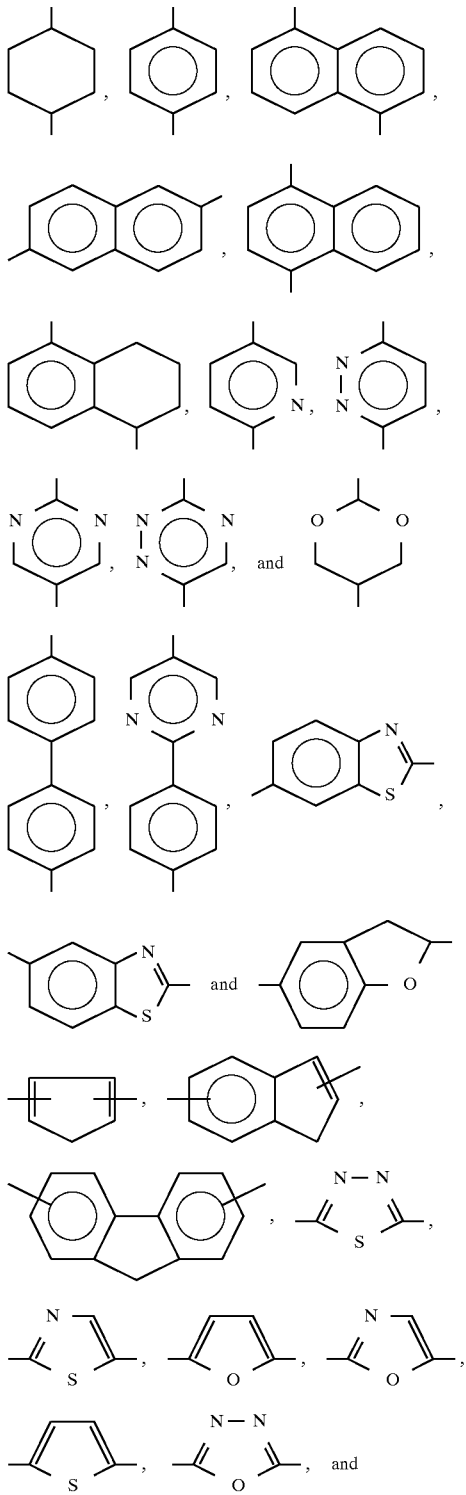

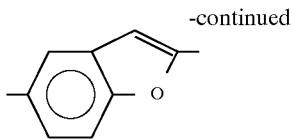

a, b, and c are each independently zero or an integer of from 1 to 3, with the proviso that the sum of a +b +c be at least 1; each A and B are non-directionally and independently selected from the group consisting of a covalent bond, —C(=O)—O—, —C(=O)—S—, —C(=O)—Se—, —C(=O)—Te—, —(CH$_2$CH$_2$)$_k$— where k is 1 to 4, —CH=CH—, —C≡C—, —CH=N—, —CH$_2$—O—,
—C(=O)—, and —O—;

each X, Y, and Z are independently selected from the group consisting of —Cl, —Br, —I, —OH, —OCH$_3$, —CH$_3$, —CF$_3$, —OCF$_3$, —CN, and —NO$_2$;

each l, m, and n are independently zero or an integer of 1 to 4;

D is a moiety selected from the group consisting of a covalent bond, —CH=CH—, and —C≡C—;

R is selected from the group consisting of

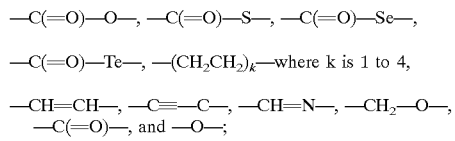

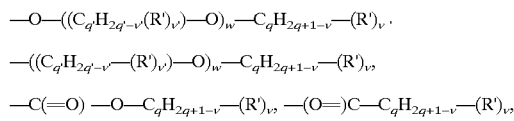

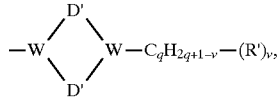

where each R' is independently selected from the group consisting of —Cl, —F, —CF$_3$, —NO$_2$, —CN, —H, —C$_q$H$_{2q+1}$, —O—(O=)C—C$_q$H$_{2q+1}$, —C(=O)—O—C$_q$H$_{2q+1}$, —Br, —OH, and —OC$_q$H$_{2q+1}$; q' is independently an integer of 1 to about 20 for each (C$_q$H$_{2q'}$—O) ; q is an integer of 1 to about 20; w is an integer of 0 to about 10 ; v is an integer of 0 to about 6; each v' is independently an integer of 0 to about 6; g is an integer of 1 to about 3; each D' is independently and non-directionally selected from the group consisting of a covalent bond,

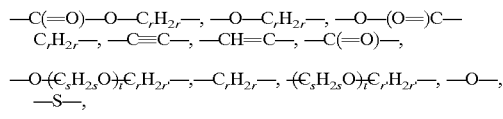

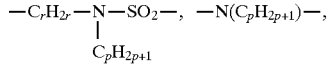

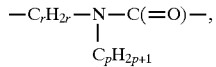

r and r' are independently integers of 0 to about 20, s is independently an integer of 1 to about 10 for each ($C_sH_{2s}O$), t is an integer of 1 to about 6, and p is an integer of 0 to about 4, with the proviso that the ring containing D' has from about 3 to about 10 ring atoms; each W is independently selected from the group consisting of N, CR', and SiR';

$R_h$ is an alkylene group having at least two carbon atoms and containing at least: one catenary ether oxygen atom; and $R_f$ is fluoroalkyl or fluoroether.

19. The compounds of claim 18 wherein said $R_f$ is perfluoroalkyl or perfluoroether and contains from 1 to about 20 carbon atoms and said $R_h$ contains from 2 to about 14 carbon atoms.

20. The compounds of claim 19 wherein said $R_h$ contains from 2 to about 10 carbon atoms.

21. The compounds of claim 18 wherein said $R_h$ is represented by the general formula $(C_sH_{2s}O)_tC_rH_{2r'}-$, wherein s is independently an integer of 1 to about 10 for each ($C_sH_{2s}O$), t is an integer of 1 to about 6, and r' is an integer of 1 to about 10.

22. The compounds of claim 21 wherein said s is an integer of about 2 to about 7, said t is an integer of 1 to about 3, and said r' is an integer of 1.

23. The compounds of claim wherein said $R_f$ is represented by the formula $-C_qF_{2q}X'$, where q is as defined in claim 17 and X' is hydrogen or fluorine.

24. The compounds of claim 18 wherein said $R_f$ is represented by the formula $-R_{f'}-R_{h'}$, where $R_{f'}$ is a linear or branched, perfluorinated or partially-fluorinated alkylene group having from 1 to about 10 carbon atoms and optionally containing one or more catenary ether oxygen atoms, and $R_{h'}$ is a linear or branched alkyl group having from 1 to about 14 carbon atoms and optionally containing one or more catenary ether oxygen atoms.

25. The compounds of claim 18 wherein said $R_f$ is represented by the formula $-(C_xF_{2x}O)_zC_yF_{2y+1}$, where x is independently an integer of 1 to about 10 for each ($C_xF_{2x}O$), y is an integer of 1 to about 10, and z is an integer of 1 to about 10.

26. The compounds of claim 18 wherein $R_h$ is represented by the directional general formula $-(C_sH_{2s}O)_tC_rH_{2r'}-$, wherein s is independently an integer of 2 to about 10 for each ($C_sH_{2s}O$), t is an integer of 1 to about 6, and r' is an integer of 1 to about 10; and $R_f$ is fluoroether; with the proviso that the compounds exhibit at least one tilted smectic mesophase.

27. The compounds of claim 18 wherein M is pyrimidine; N is phenyl; A and B are each a covalent bond; a and b are integers of 1; c is zero; l is an integer of 2; m is an integer of 4; R is an alkyl, fluoroalkyl, alkoxy, or fluoroalkoxy group having from about 4 to about 8 carbon atoms and optionally containing one or more catenary ether oxygen atoms; $R_h$ has from about 4 to about 10 carbon atoms and is represented by the directional general formula $-(C_sH_{2s}O)_tC_rH_{2r'}-$, wherein s is independently an integer of 3 to about 7 for each ($C_sH_{2s}O$), t is an integer of 1 to 2, and r' is an integer of 1; and $R_f$ is a perfluoroether group represented by the formula $-(C_xF_{2x}O)_zC_yF_{2y+1}$, where x is independently an integer of 1 to about 10 for each ($C_xF_{2x}O$), y is an integer of 1 to about 10, and z is an integer of 1 to about 10; with the proviso that the compounds exhibit at least one tilted smectic mesophase.

28. The compounds of claim 18 wherein $R_h$ is represented by the directional general formula $-(C_sH_{2s}O)_tC_rH_{2r'}-$, wherein s is independently an integer of 3 to about 10 for each ($C_sH_{2s}O$), t is an integer of 1 to about 6, and r' is an integer of 1 to about 10; and $R_f$ is fluoroether; with the proviso that the compounds do not exhibit at least one tilted smectic mesophase.

29. The compounds of claim 18 wherein M is pyrimidine; N is phenyl; A and B are each a covalent - bond; a and b are integers of 1; c is zero; l is an integer of 2; m is an integer of 4; R is an alkyl, fluoroalkyl, alkoxy, or fluoroalkoxy group having from about 4 to about 8 carbon atoms and optionally containing one or more catenary ether oxygen atoms; $R_h$ has from about 4 to about 10 carbon atoms and is represented by the directional general formula $-(C_sH_{2s}O)_tC_rH_{2r'}-$, wherein s is independently an integer of 3 to about 7 for each ($C_sH_{2s}O$), t is an integer of 1 to 2, and r' is an integer of 1; and $R_f$ is a perfluoroether group represented by the formula $-(C_xF_{2x}O)_zC_yF_{2y+1}$, where x is independently an integer of 1 to about 10 for each ($C_xF_{2x}O$), y is an integer of 1 to about 10, and z is an integer of 1 to about 10; with the proviso that the compounds do not exhibit at least one tilted smectic mesophase.

30. A mixture of liquid crystal Compounds comprising at least one compound of claim 18.

31. A liquid crystal display device containing the mixture of claim 30.

32. A process for controlling the cone tilt angle of a tilted smectic liquid crystal composition comprising the step of combining (a) at least one liquid crystal composition comprising at least one smectic or latent smectic liquid crystal compound comprising (i) an aliphatic fluorocarbon terminal portion represented by the formula $-D-R_h-R_f$, where $R_h$ contains from 2 to about 14 carbon atoms and is represented by the general formula $(C_sH_{2s}O)_tC_rH_{2r'}-$, wherein s is independently an integer of 1 to about 10 for each ($C_sH_{2s}O$), t is an integer of 1 to about 6, and r' is an integer of 1 to about 10; $R_f$ is perfluoroalkyl or perfluoroether and contains from 1 to about 20 carbon atoms; and D is a moiety selected from the group consisting of a covalent bond, $-CH=CH-$, and $-C\equiv C-$; (ii) an aliphatic hydrocarbon terminal portion; and (iii) a central core connecting said terminal portions; and (b) at least one liquid crystal composition comprising at least one fluorine-containing, smectic or latent smectic liquid crystal compound; with the provisos that at least one of said compositions (a) and (b) comprises at least one chiral liquid crystal compound and that said combining of compositions (a) and (b) provides an optically active, Lilted chiral smectic liquid crystal composition.

33. A mixture of liquid crystal compounds prepared by carrying out the process step recited in claim 32.

34. A liquid crystal display device containing the mixture of claim 33.

* * * * *

UNITED STATES PATENT AND TRADEMARK OFFICE
CERTIFICATE OF CORRECTION

PATENT NO.: 5,855,812
DATED: January 5, 1999
INVENTOR(S): Marc D. Radcliffe, Patricia M. Savu, Daniel C. Snustad, and Terence D. Spawn It is certified that error appears in the above-identified patent and that said Letters Patent is hereby corrected as shown below:

Column 1, line 31, "$(\tau=\eta\sin^2\eta/P_sE)$" should read --$(\tau=\eta\sin^2\Theta/P_sE)$--

Column 1, line 34, "$(\eta)$" should read --$(\Theta)$--

Column 1, line 49, "$\sin^2(4\eta)$" should read --$\sin^2(4\Theta)$--

Column 1, line 51, "$\eta$=liquid crystal" should read --$\Theta$=liquid crystal--

Column 1, line 54, "$\sin^2(4\eta)$" should read --$\sin^2(4\Theta)$--

Column 1, line 67, "22.5degrees" should read --22.5 degrees--

Column 2, line 19, "and at terminal" should read --and a terminal--

Column 4, line 10, "mesophase, than" should read --mesophases than--

Column 6, line 10, after the formula, --and-- should be added

Column 6, line 31, "--$C_sH_{2s}$--)t $C_rH_{2r}$--," should read -- --$C_sH_{2s}O$--)t $C_rH_{2r}$--, --

Column 6, line 32, after "--S--", the following should be added -- --$OSO_2$--, --$SO_2$--, --$SO_2$--$C_rH_{2r}$--, --

Column 6, line 40, after the formula, the following should be added, --and combinations thereof, where--

Column 6, line 61, "6 preferably," should read --6 (preferably,--

Column 7, line 29, "U.S.S.N. 08/338,96" should read --U.S.S.N. 08/338,961--

Column 10, line 4, "KristalLin-" should read -- Kristallin- --

Column 10, line 9, "Fluorin-ed" should read --Fluorinated--

UNITED STATES PATENT AND TRADEMARK OFFICE
CERTIFICATE OF CORRECTION

PATENT NO.: 5,855,812
DATED: January 5, 1999
INVENTOR(S): Marc D. Radcliffe, Patricia M. Savu, Daniel C. Snustad, and Terence D. Spawn It is certified that error appears in the above-identified patent and that said Letters Patent is hereby corrected as shown below:

Column 10, line 17, "ECE" should read --ECF--

Column 10, line 50, After "116g)", a period --.-- should be added

Column 11, line 25, "product: was" should read --product was--

Column 11, line 44, "octyk" should read --octyl--

Column 11, line 63, "(6).0 g," should read --(6.0 g,--

Column 11, line 64, "m=ol," should read --mmol,--

Column 11, line 66, "octy2." should read --octyl--

Column 14, line 57, "octyl-$^2$-($^4$-" should read -- octyl-2-(4- --

Column 15, line 34, "the. crude" should read --the crude--

Column 16, line 24, "0.31" should read --0.01--

Column 17, line 35, "2difluoroethoxy)" should read --difluoroethoxy--

Column 17, line 46, "phe2nyl" should read --phenyl--

Column 17, line 49, "(4 mL)" should read --(5 mL)--

Column 20, line 67, "+30°C." should read -- -30°C.--

Column 23, line 19, "C=C" should read --C≡C--

Column 29, line 29, "-2,2,3,.3,4,4" should read -- -2,2,3,3,4,4--

UNITED STATES PATENT AND TRADEMARK OFFICE
CERTIFICATE OF CORRECTION

PATENT NO.: 5,855,812

DATED: January 5, 1999

INVENTOR(S): Marc D. Radcliffe, Patricia M. Savu, Daniel C. Snustad, and Terence D. Spawn It is certified that error appears in the above-identified patent and that said Letters Patent is hereby corrected as shown below:

Column 31, line 48, "$-((C_{q'}H_{2q'-v}-,-O)_w-(R')_v$" should read -- $-((C_{q'}H_{2q'-v}-(R')_v)-O)_w-C_qH_{2q+1-v}-(R')_v$ --

Column 31, line 54, insert --and-- after formula

Column 31, line 63, "$=O=C_qH_{2q+1}$," should read -- $-O-C_qH_{2q+1}$, --

Column 32, line 5, "$C=C_rH_{2r}-$," should read -- $C-C_rH_{2r}-$, --

Column 32, line 7, "$-C_rH_{2r}-$" should read -- $C_rH_{2r}-$ --

Column 32, line 9, after "$-S-$," the following should be added -- $-OSO_2-$, $-SO_2-$, $-SO_2-C_rH_{2r}-$, --

Column 32, line 12, the following should be added, -- $-CH=N-$, and combinations thereof, where --

Column 32, line 18, "]" should read --1--

Column 34, line 17, "$-C=-C-$," should read -- $-C\equiv C-$ --

Column 34, line 21, After "$-Cl$," insert -- $-F$, --

Column 34, line 36, insert --and-- after formula

Column 34, line 58, after "$-S-$," the following should be added -- $-OSO_2-$, $-SO_2-$, $-SO_2-C_rH_{2r}-$, --

Column 34, line 65, The following should be added -- $-CH=N-$, and combinations thereof, where --

Column 35, line 7, "least: one" should read --least one--

Column 35, line 24, "claim wherein" should read --claim 18 wherein--

Column 35, line 26, "claim 17" should read --claim 18--

UNITED STATES PATENT AND TRADEMARK OFFICE
CERTIFICATE OF CORRECTION

PATENT NO.: 5,855,812
DATED: January 5, 1999
INVENTOR(S): Marc D. Radcliffe, Patricia M. Savu, Daniel C. Snustad, and Terence D. Spawn It is certified that error appears in the above-identified patent and that said Letters Patent is hereby corrected as shown below:

Column 35, line 36, "$-C_xF_{2x}O)_zC_yF_{2y+1},$" should read -- $-C_xF_{2x}O)_zC_yF_{2y+1},$ --

Column 36, line 12, "covalent - bond" should read --covalent bond--

Column 36, line 27, "Compounds" should read --compounds--

Column 36, line 38, "$C_sH_{2s}O)_tC_rH_{2r}'-$" should read -- $C_sH_{2s}O)_tC_rH_{2r}-$ --

Column 36, line 51, "lilted" should read --tilted--

Signed and Sealed this

Twentieth Day of March, 2001

Attest:

NICHOLAS P. GODICI

*Attesting Officer*     *Acting Director of the United States Patent and Trademark Office*